United States Patent
Batra et al.

(10) Patent No.: US 12,162,853 B2
(45) Date of Patent: Dec. 10, 2024

(54) SYNTHESIS OF ESUBERAPROST PRODRUGS

(71) Applicant: United Therapeutics Corporation, Silver Spring, MD (US)

(72) Inventors: Hitesh Batra, Herndon, VA (US); Liang Guo, Vienna, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 129 days.

(21) Appl. No.: 18/100,330

(22) Filed: Jan. 23, 2023

(65) Prior Publication Data

US 2023/0159480 A1    May 25, 2023

Related U.S. Application Data

(62) Division of application No. 17/287,320, filed as application No. PCT/US2019/056663 on Oct. 17, 2019, now Pat. No. 11,560,363.

(60) Provisional application No. 62/748,759, filed on Oct. 22, 2018.

(51) Int. Cl.
    *C07D 307/93*    (2006.01)
(52) U.S. Cl.
    CPC ................ *C07D 307/93* (2013.01)
(58) Field of Classification Search
    CPC .................................................... C07D 307/93
    See application file for complete search history.

(56) References Cited

U.S. PATENT DOCUMENTS

| 5,202,447 A | 4/1993 | Ohno et al. |
| 7,345,181 B2 | 3/2008 | Kim et al. |
| 8,779,170 B2 | 7/2014 | Sharma et al. |
| 9,765,047 B2 | 9/2017 | Batra et al. |
| 9,913,912 B2 | 3/2018 | Rau et al. |
| 10,093,641 B2 | 10/2018 | Batra et al. |
| 10,421,737 B2 | 9/2019 | Hortobã Gyi et al. |
| 11,560,363 B2 * | 1/2023 | Batra .................. C07D 307/93 |

FOREIGN PATENT DOCUMENTS

| WO | WO-2015/179427 A1 | 11/2015 |
| WO | WO-2017/027706 A1 | 2/2017 |

OTHER PUBLICATIONS

Batra et al., STN International, CAPLUS database, Columbus (Ohio), 2017, accession No. 2017:272713.
Hortobagyi et al., STN International, CAPLUS database, Columbus (Ohio), 2017, accession No. 2017:1632155.
Nagase et al,. "Synthesis of ( )-5,6,7-Trinor-4,8-Inter-m-Phenylene PGI2'1," Tetrahedron Letters, 1990, 31(31):4493-4494.

* cited by examiner

*Primary Examiner* — Golam M Shameem
(74) *Attorney, Agent, or Firm* — Foley & Lardner LLP

(57) ABSTRACT

Provided are novel prodrugs of esuberaprost and pharmaceutical compositions thereof, as well as methods of making and methods of using these prodrugs.

5 Claims, 15 Drawing Sheets

SYNTHESIS OF ESUBERAPROST PRODRUGS

CROSS-REFERENCE TO RELATED APPLICATION

This Application claims priority to U.S. Provisional Patent Application No. 62/748,759, filed Oct. 22, 2018, which application is incorporated herein by reference in its entirety.

FIELD

The present application relates to prostacyclins and more particularly, to prodrugs of esuberaprost, pharmaceutical compositions thereof, and to methods of making and using such prodrugs and pharmaceutical compositions.

BACKGROUND

Prostacyclin derivatives are useful pharmaceutical compounds possessing activities such as platelet aggregation inhibition, gastric secretion reduction, lesion inhibition, and bronchodilation Beraprost is a synthetic benzoprostacyclin analogue of natural prostacyclin that is currently under clinical trials for the treatment of pulmonary hypertension and vascular disease (excluding renal disease) in North America and Europe. Esuberaprost is a reformulated single isomer of beraprost currently being developed for the treatment of pulmonary arterial hypertension and vascular disease.

Beraprost and related benzoprostacyclin analogues are disclosed in U.S. Pat. No. 5,202,447 and Tetrahedron Lett. 31, 4493 (1990). Furthermore, as described in U.S. Pat. No. 7,345,181, several synthetic methods are known to produce benzoprostacyclin analogues, including the pharmacologically active isomer of beraprost, such as beraprost 314-d (esuberaprost).

Derivatives and prodrugs of existing drugs have the ability to improve the physicochemical properties of such drugs. Therefore, it is desired to prepare improved esuberaprost compounds, such as prodrugs, and develop efficient, commercially applicable synthetic methods to the prodrugs of esuberaprost.

SUMMARY

An object of the present invention is to provide prodrugs of esuberaprost, pharmaceutical compositions thereof, process for selectively producing prodrugs of esuberaprost, and methods of using prodrugs of esuberaprost and pharmaceutical compositions thereof to treat various diseases or disorders.

At least one embodiment may be a compound the Formula (I), or a diastereomer, enantiomer or pharmaceutically acceptable salt of the compound:

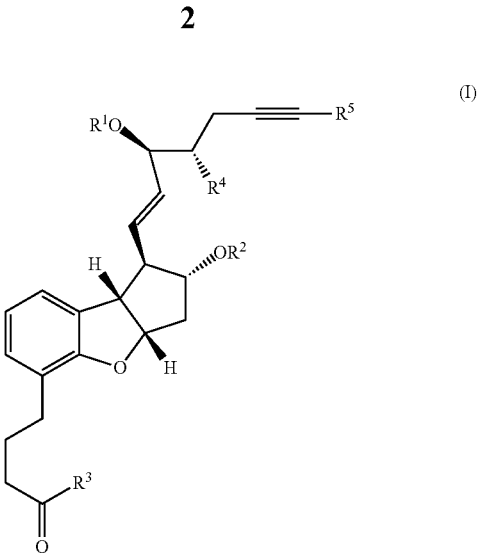

wherein $R^1$ and $R^2$ each independently represent H, $C_1$-$C_6$ alkyl, —$CO_2R^6$, —$CONR^6R^7$, —$P(O)(OH)_2$—, —$(CH_2)_2OP(O)(OH)_2$— or a hydroxy protecting group, or wherein $OR^1$ or $OR^2$ forms an ester of an amino acid, or wherein $R^1$ and $R^2$ connected to carbonyl to make a cyclic carbonate group, or wherein $OR^1$ or $OR^2$ together form a phosphate group;

$R^3$ represents $NR^7R^8$, $OR^9$, or $NHSO_2R^{10}$;

$R^4$ represents H or $C_{1-3}$ alkyl;

$R^5$, $R^6$ and $R^7$ each independently represent H or $C_{1-6}$ alkyl, or wherein $R^6$ and $R^7$ together with the nitrogen to which they are attached form a piperidine or a bipiperidine ring;

$R^8$ represents H, optionally substituted $C_1$-$C_6$ alkyl, or

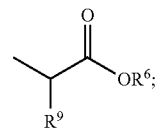

or wherein $R^7$ and $R^8$ are such that $NR^7R^8$ is an amide of an amino acid;

$R^9$ represents H or $C_1$-$C_6$ alkyl, which may be optionally substituted with a terminal hydroxyl or carboxy group; and $R^{10}$ represents H, optionally substituted $C_1$-$C_6$ alkyl, optionally substituted $C_6$-$C_{10}$ aryl, optionally substituted $C_3$-$C_8$ heteroaryl or optionally substituted heterocyclyl;

with a proviso that all of $R^1$, $R^2$ and $R^8$ are not H.

Yet another embodiment is a compound or a pharmaceutically acceptable salt thereof, wherein the compound having one of the following formulas:

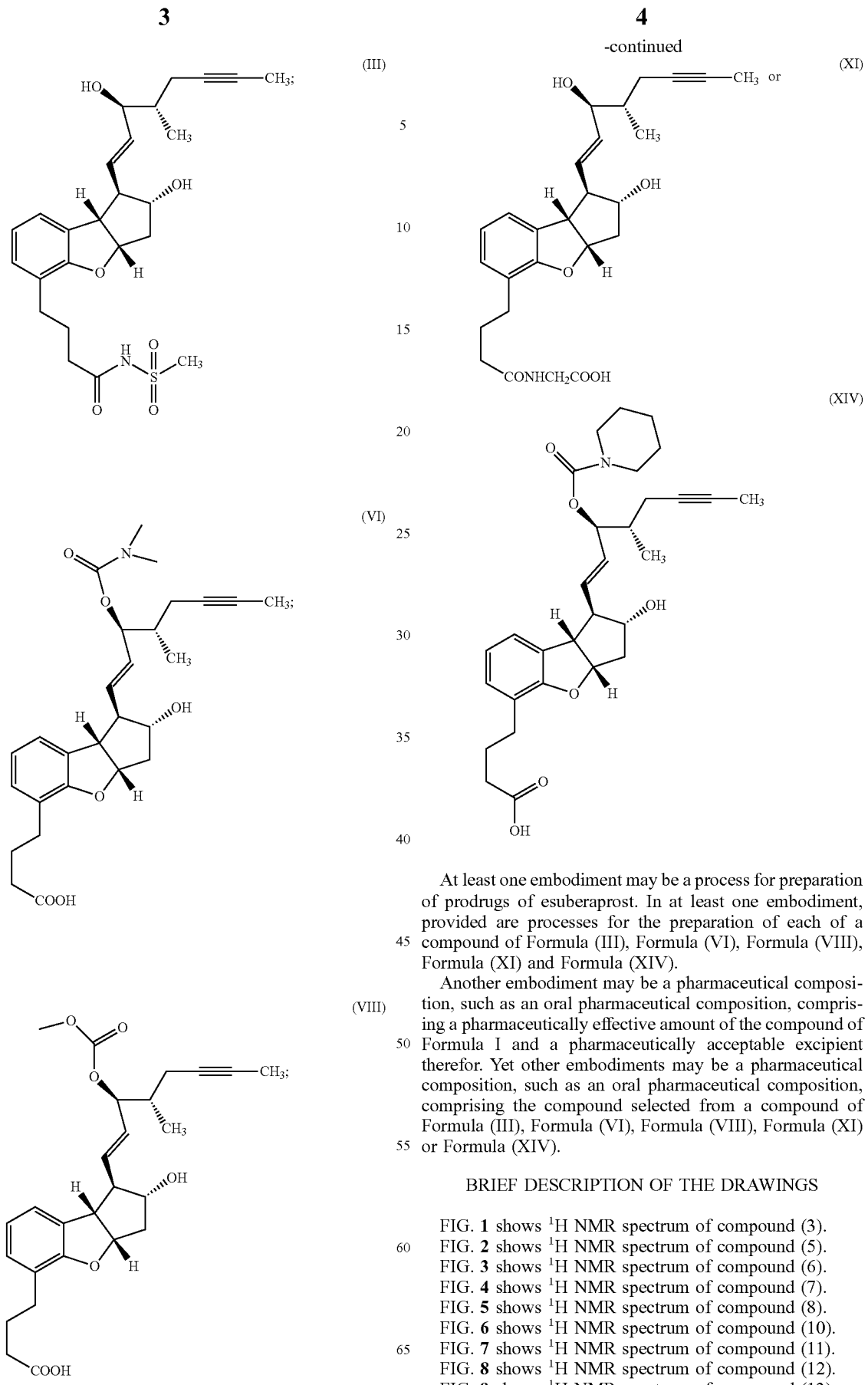

At least one embodiment may be a process for preparation of prodrugs of esuberaprost. In at least one embodiment, provided are processes for the preparation of each of a compound of Formula (III), Formula (VI), Formula (VIII), Formula (XI) and Formula (XIV).

Another embodiment may be a pharmaceutical composition, such as an oral pharmaceutical composition, comprising a pharmaceutically effective amount of the compound of Formula I and a pharmaceutically acceptable excipient therefor. Yet other embodiments may be a pharmaceutical composition, such as an oral pharmaceutical composition, comprising the compound selected from a compound of Formula (III), Formula (VI), Formula (VIII), Formula (XI) or Formula (XIV).

DETAILED DESCRIPTION

Figure 1:
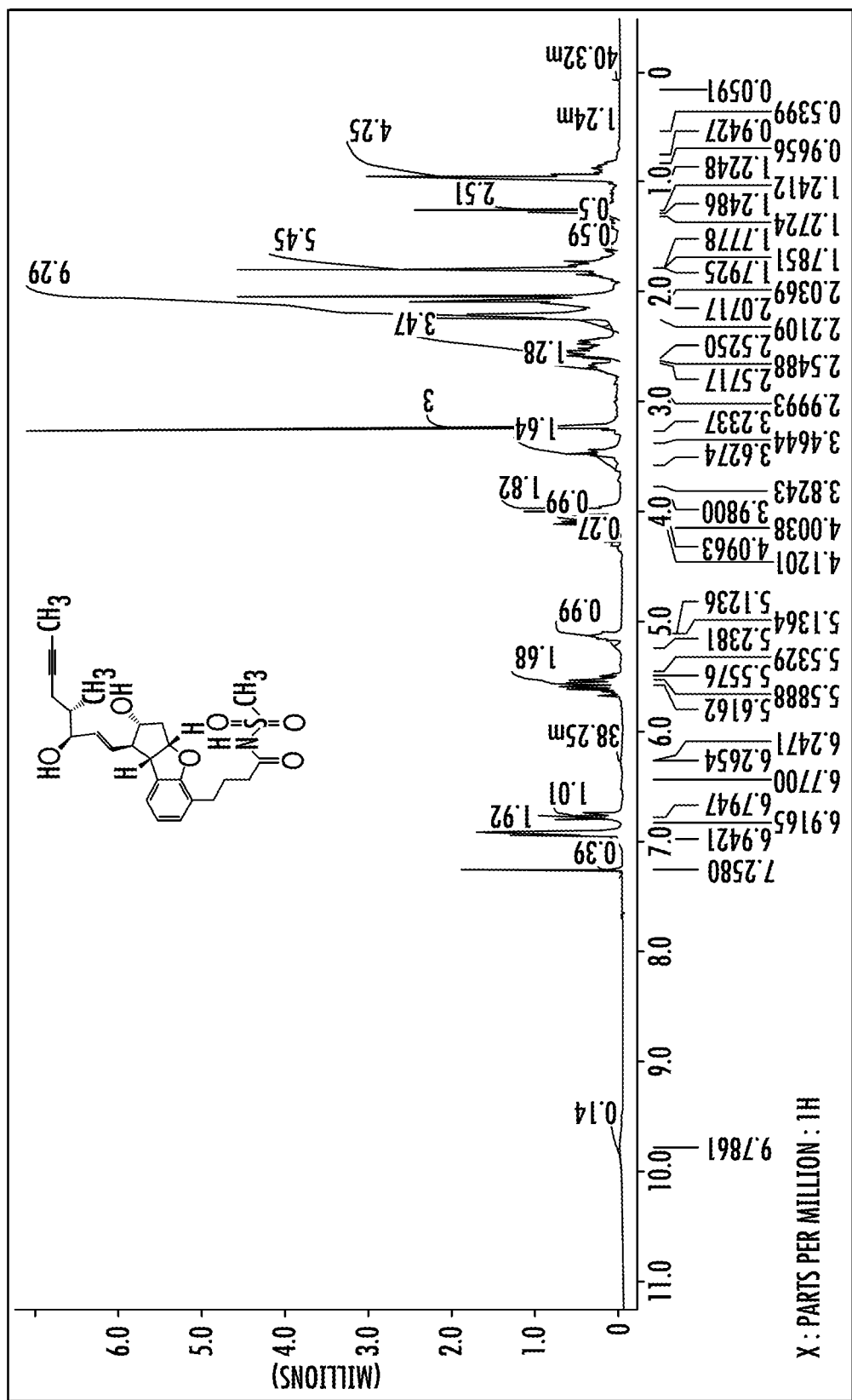
FIG. 1 shows $^1$H NMR spectrum of compound (3).
Figure 2:
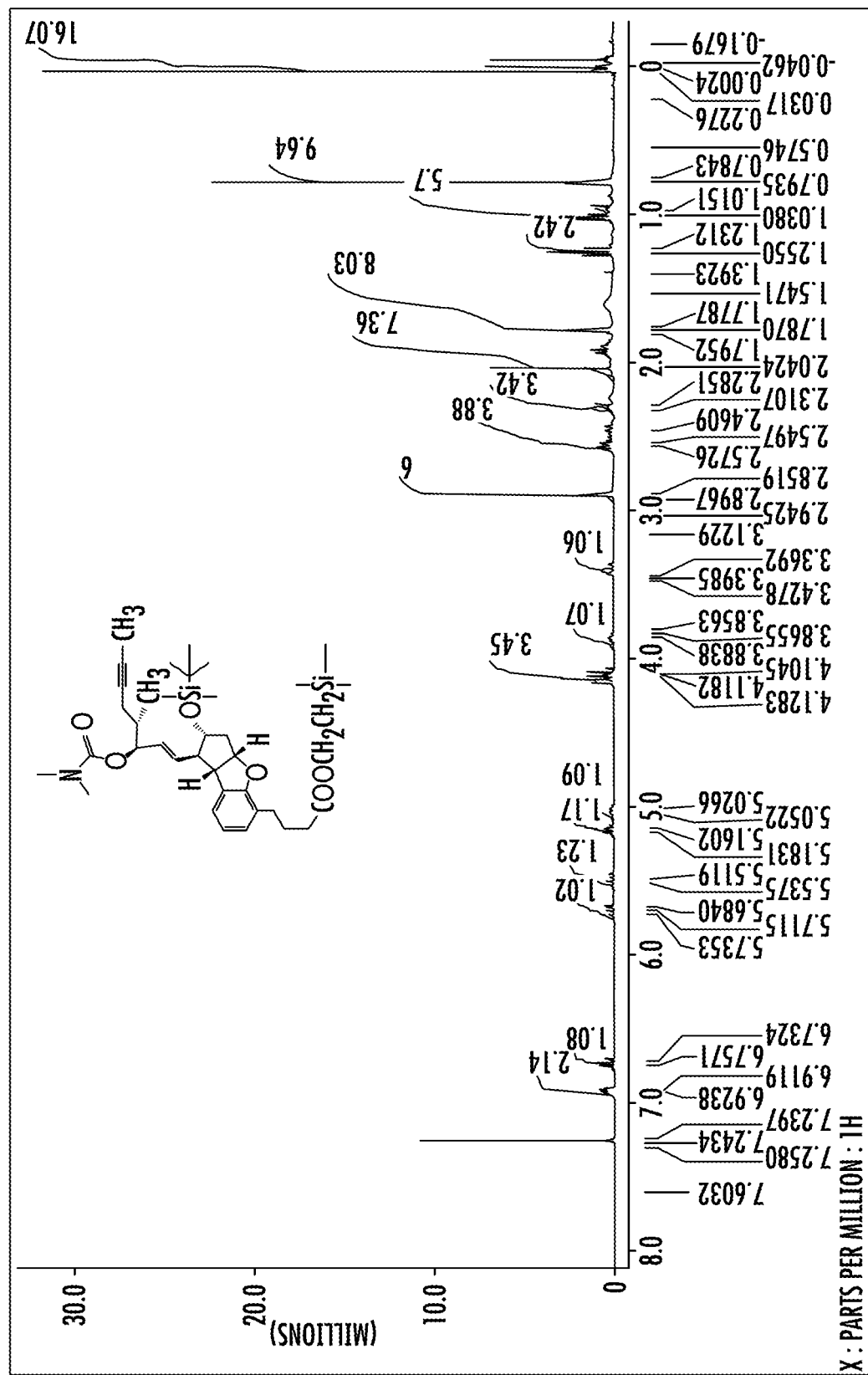
FIG. 2 shows $^1$H NMR spectrum of compound (5).
Figure 3:
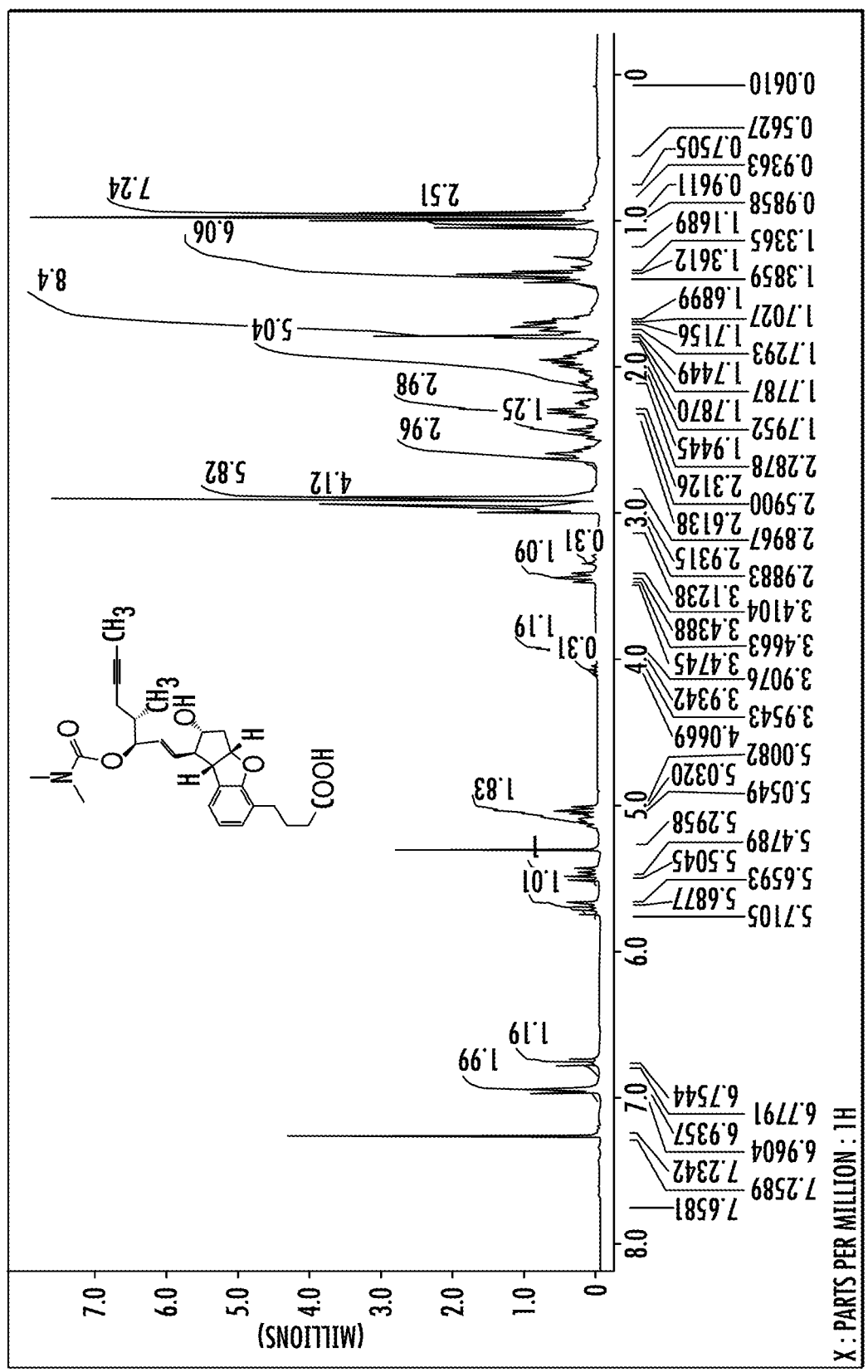
FIG. 3 shows $^1$H NMR spectrum of compound (6).
Figure 4:
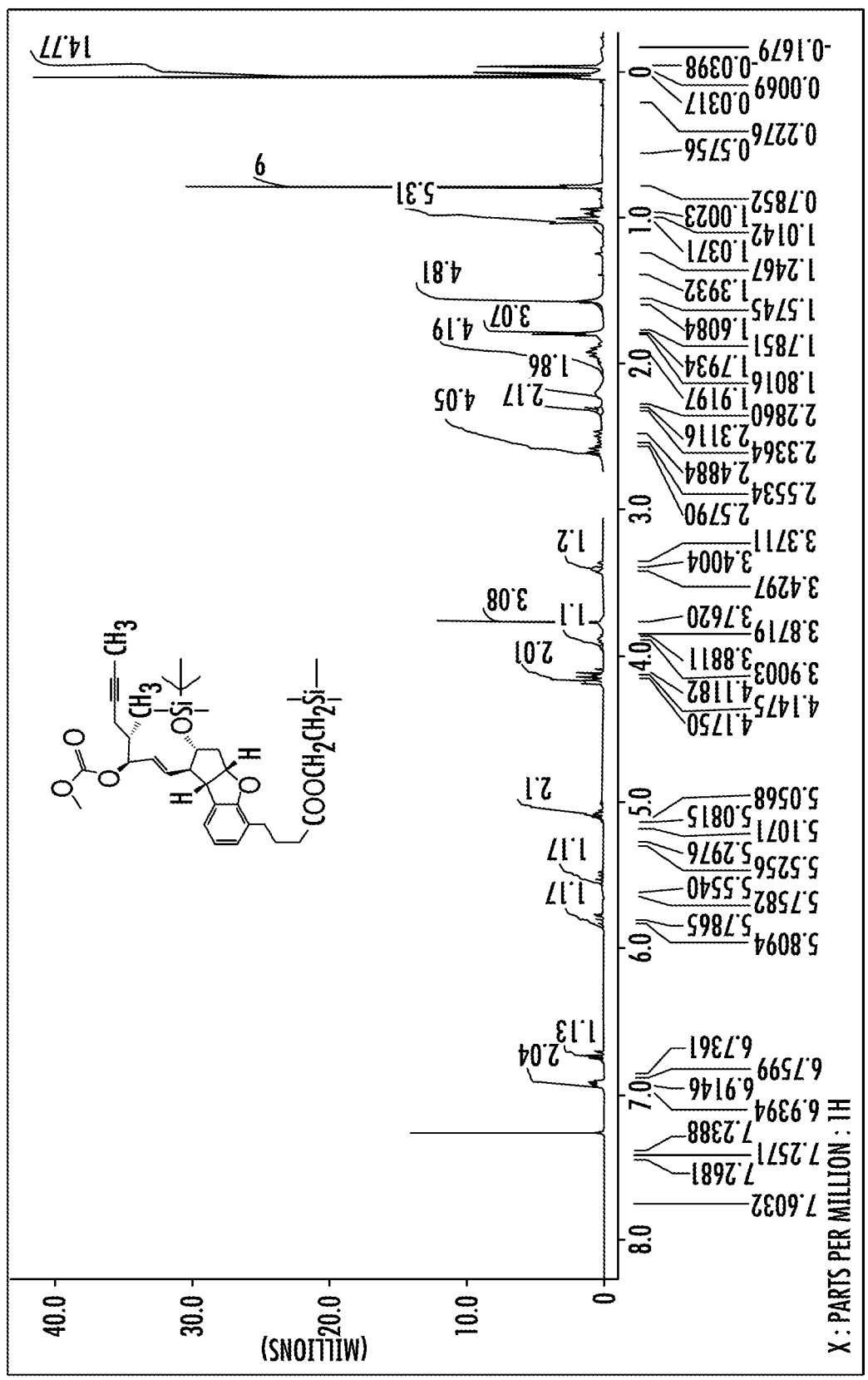
FIG. 4 shows $^1$H NMR spectrum of compound (7).
Figure 5:
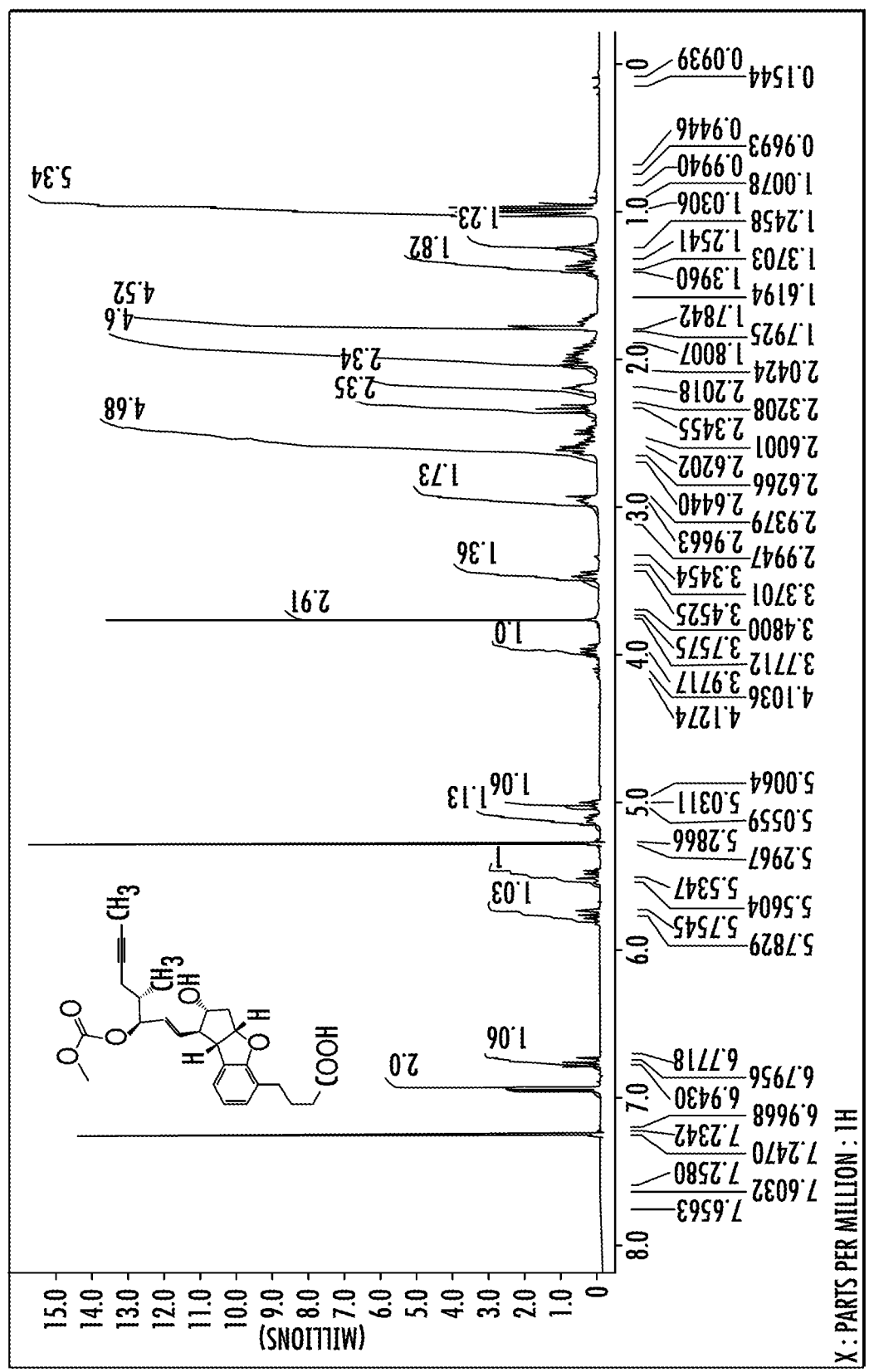
FIG. 5 shows $^1$H NMR spectrum of compound (8).
Figure 6:
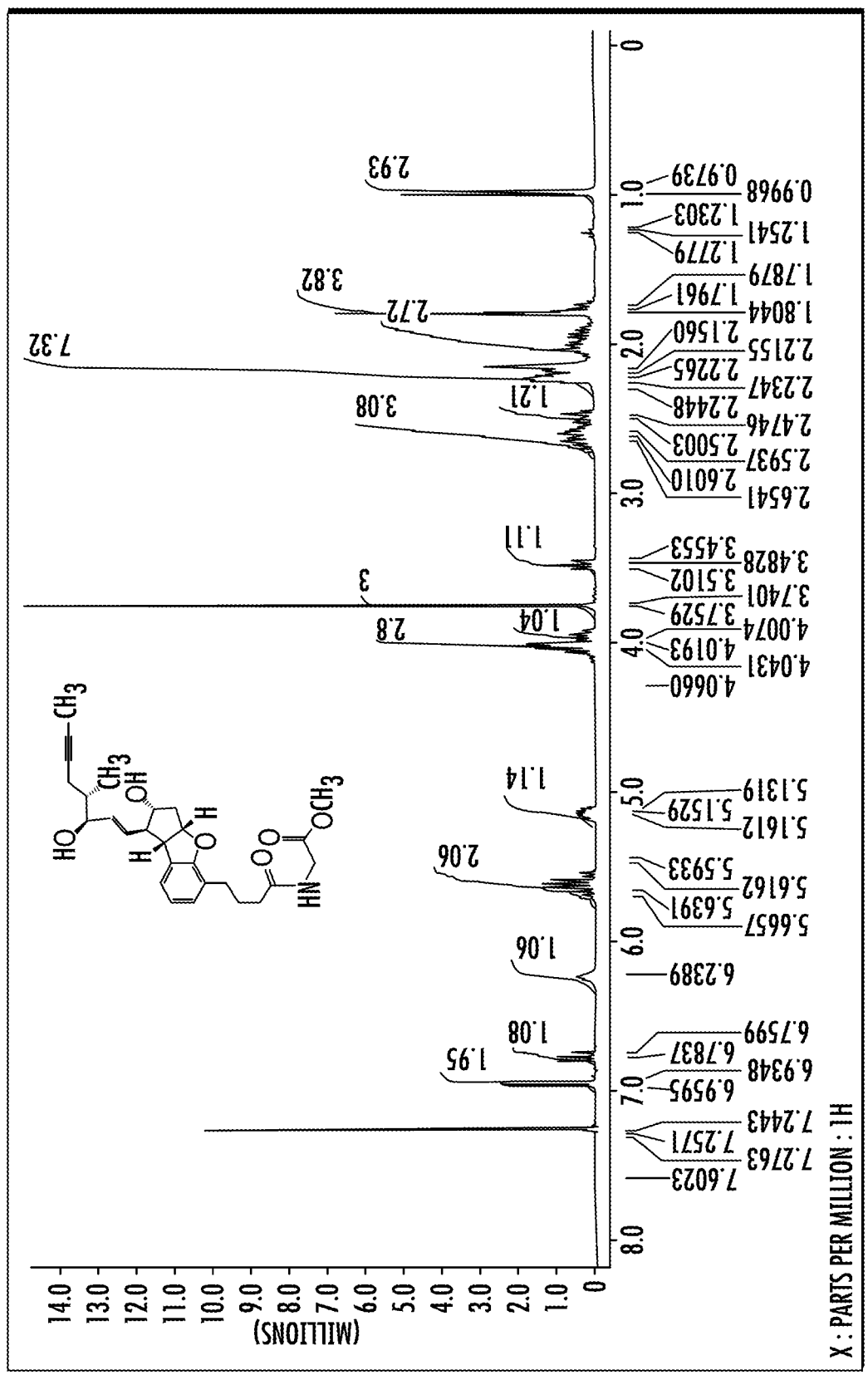
FIG. 6 shows $^1$H NMR spectrum of compound (10).
Figure 7:
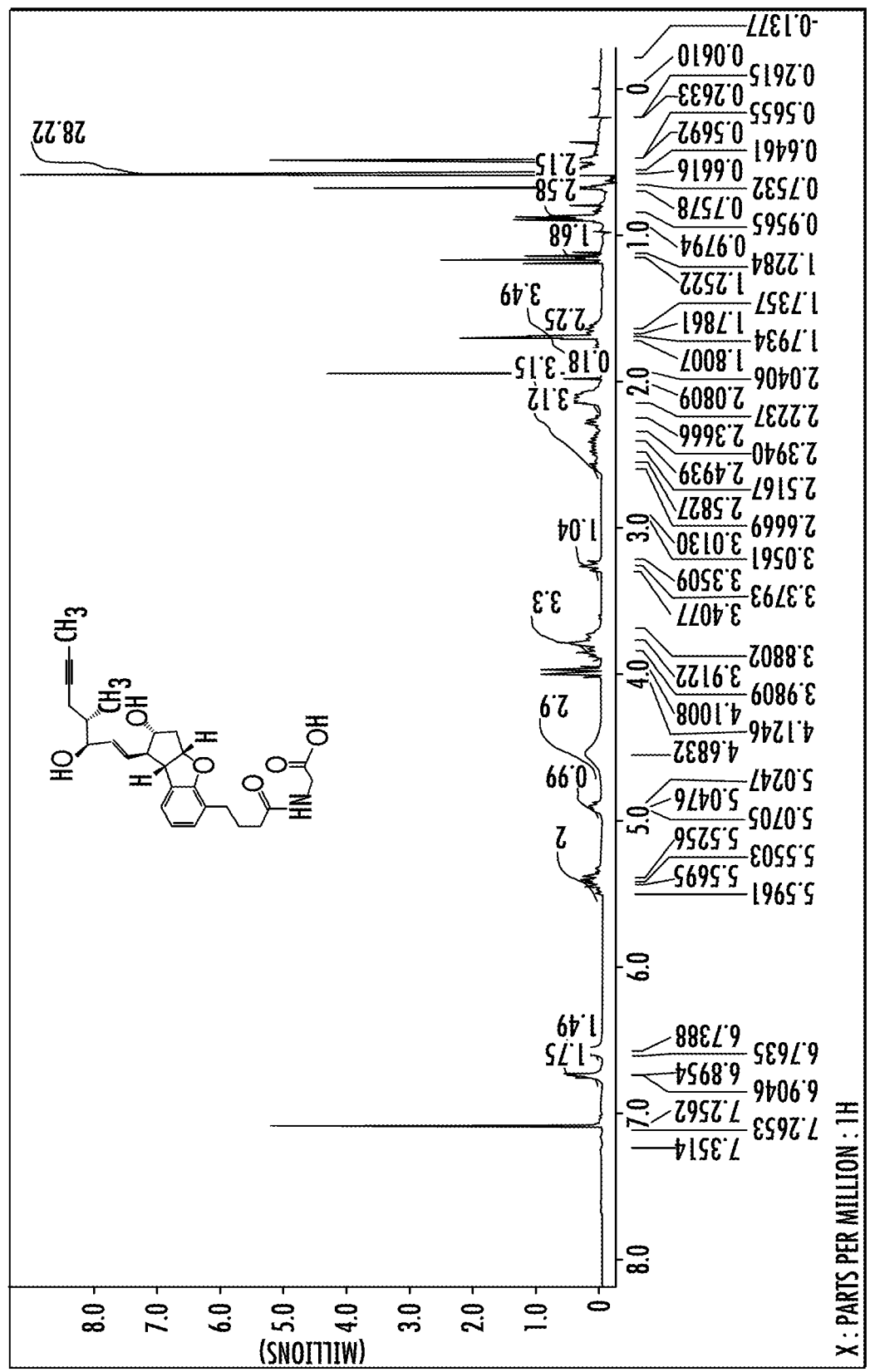
FIG. 7 shows $^1$H NMR spectrum of compound (11).
Figure 8:
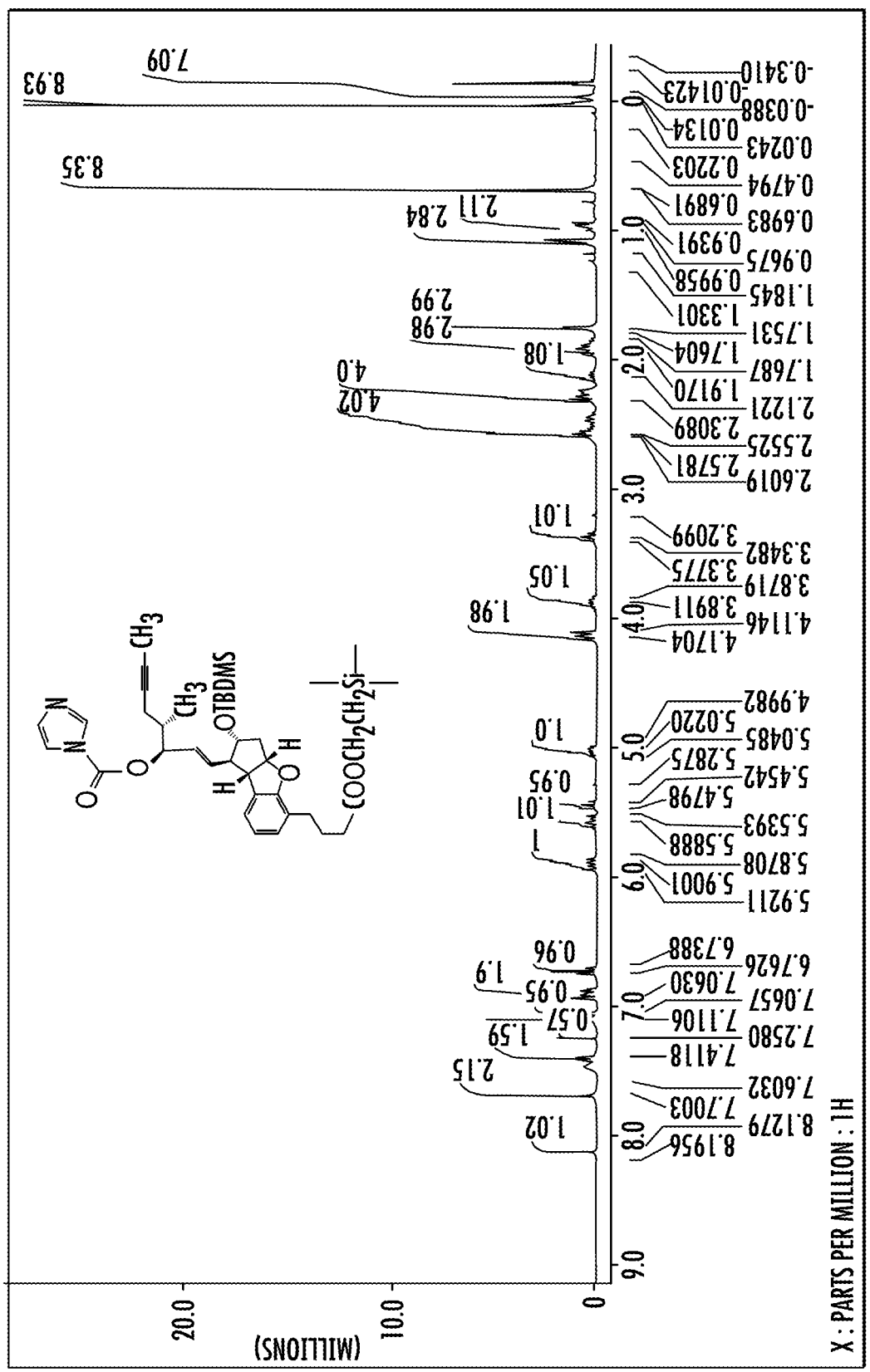
FIG. 8 shows $^1$H NMR spectrum of compound (12).
Figure 9:
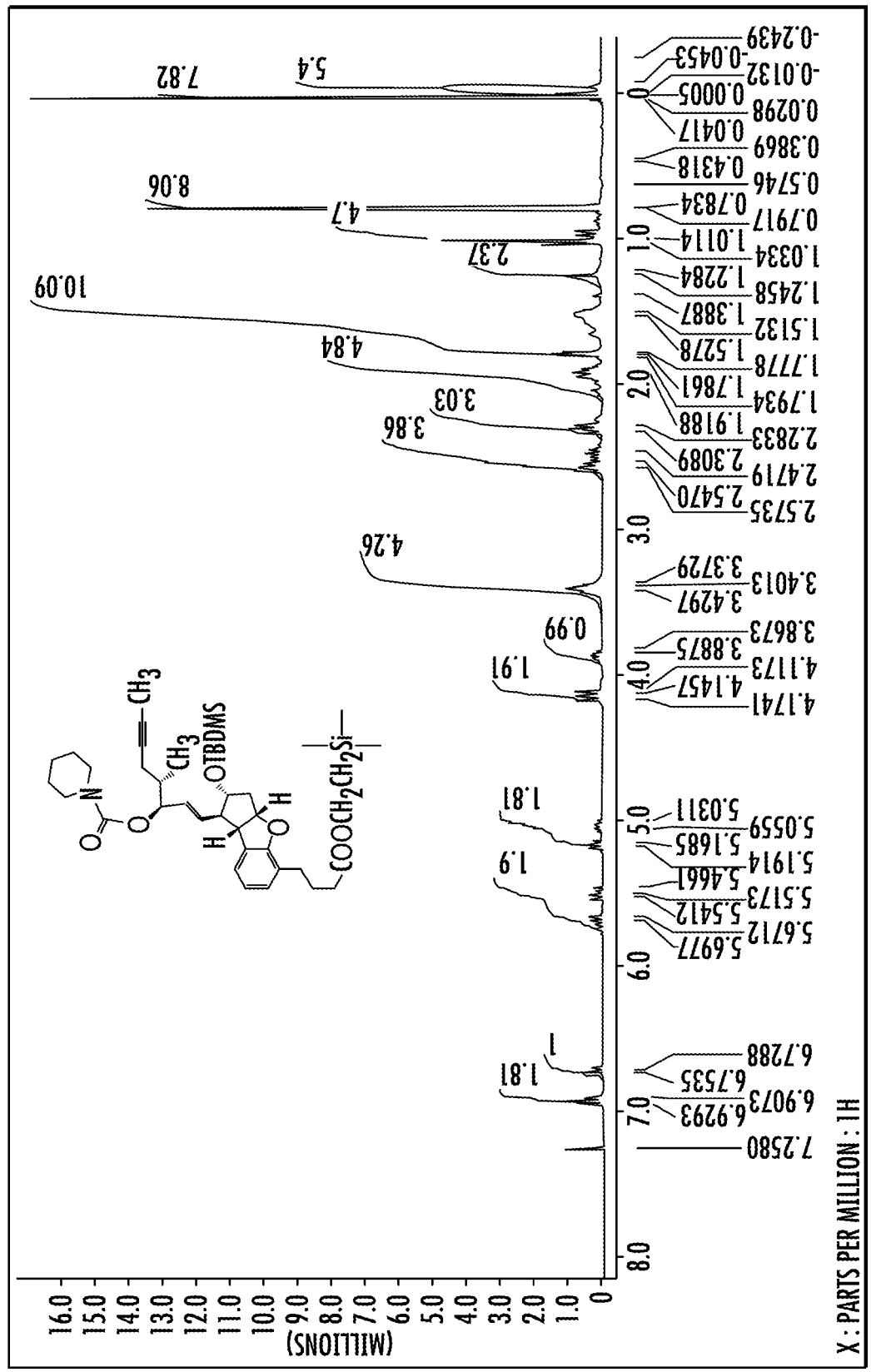
FIG. 9 shows $^1$H NMR spectrum of compound (13).
Figure 10:
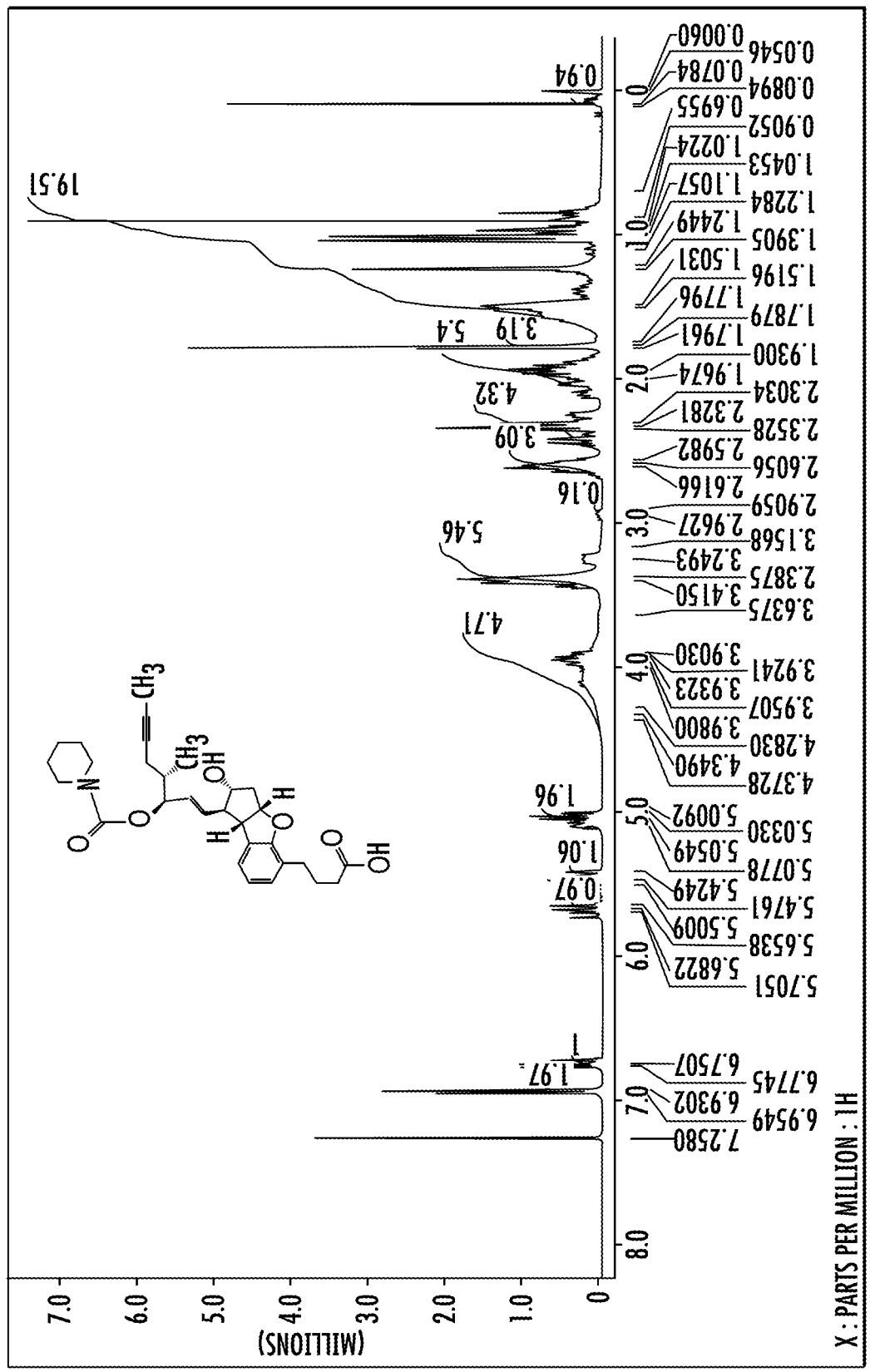
FIG. 10 shows $^1$H NMR spectrum of compound (14).
Figure 11:
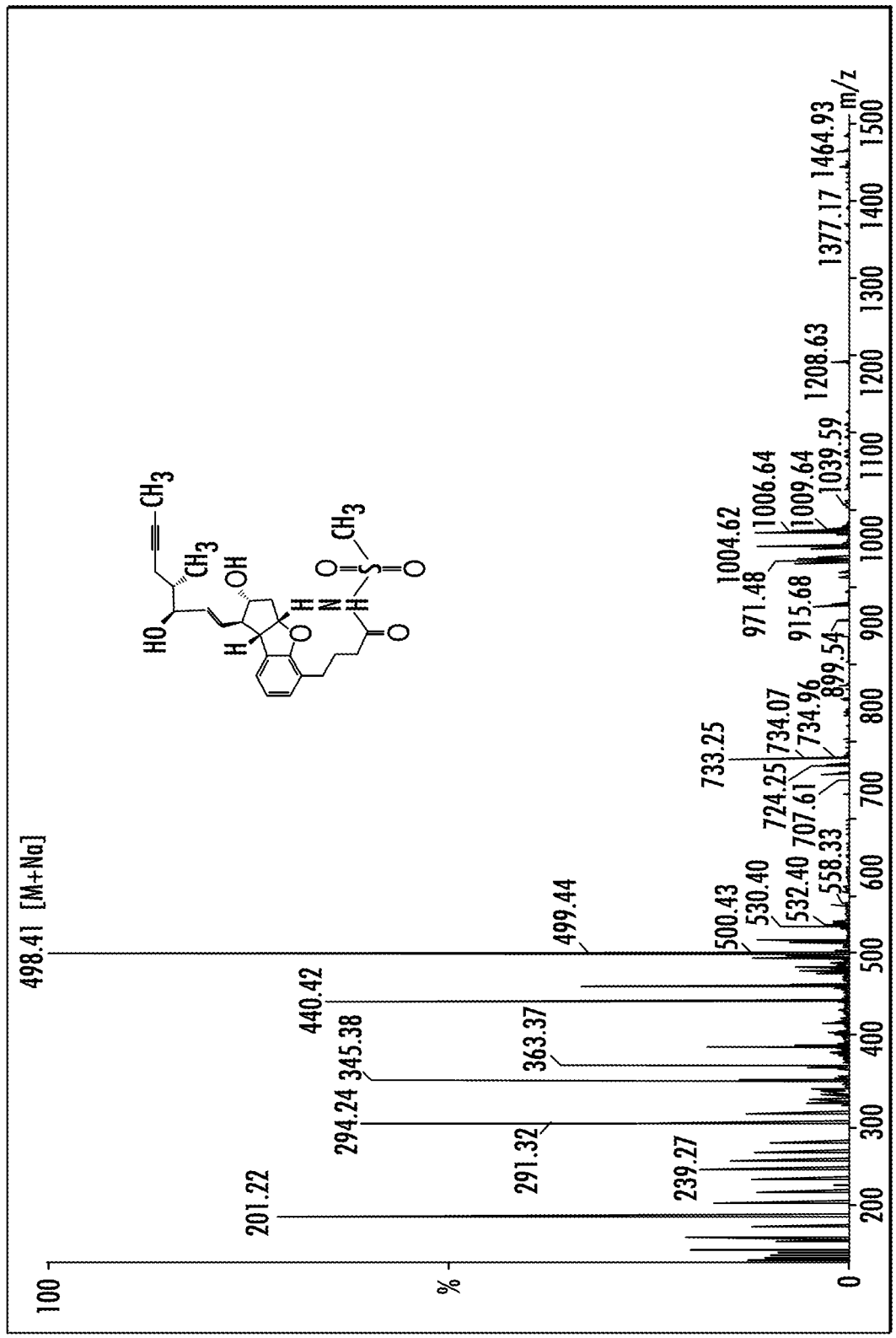
FIG. 11 shows mass spectrum of compound (3).
Figure 12:
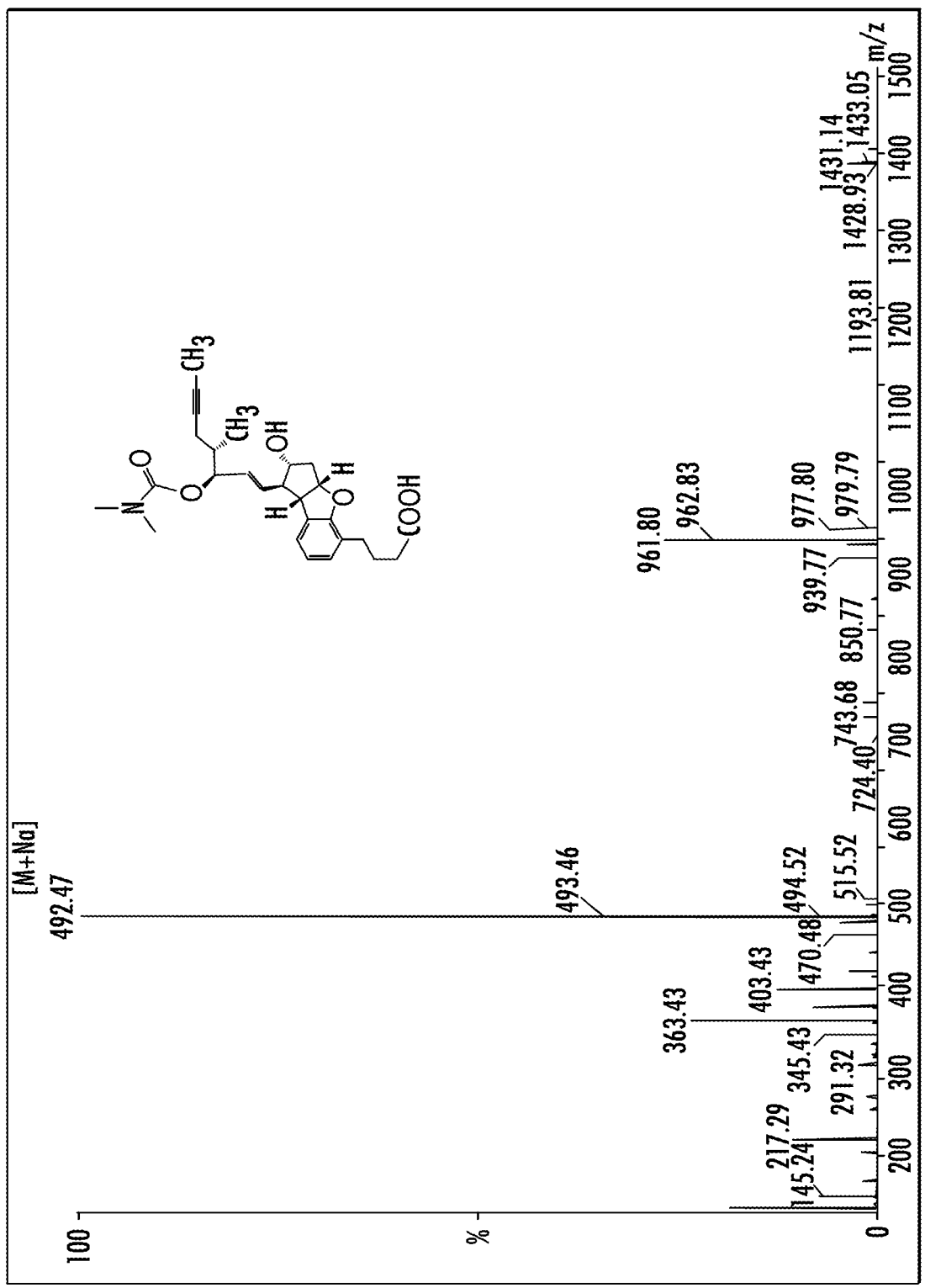
FIG. 12 shows mass spectrum of compound (6).
Figure 13:
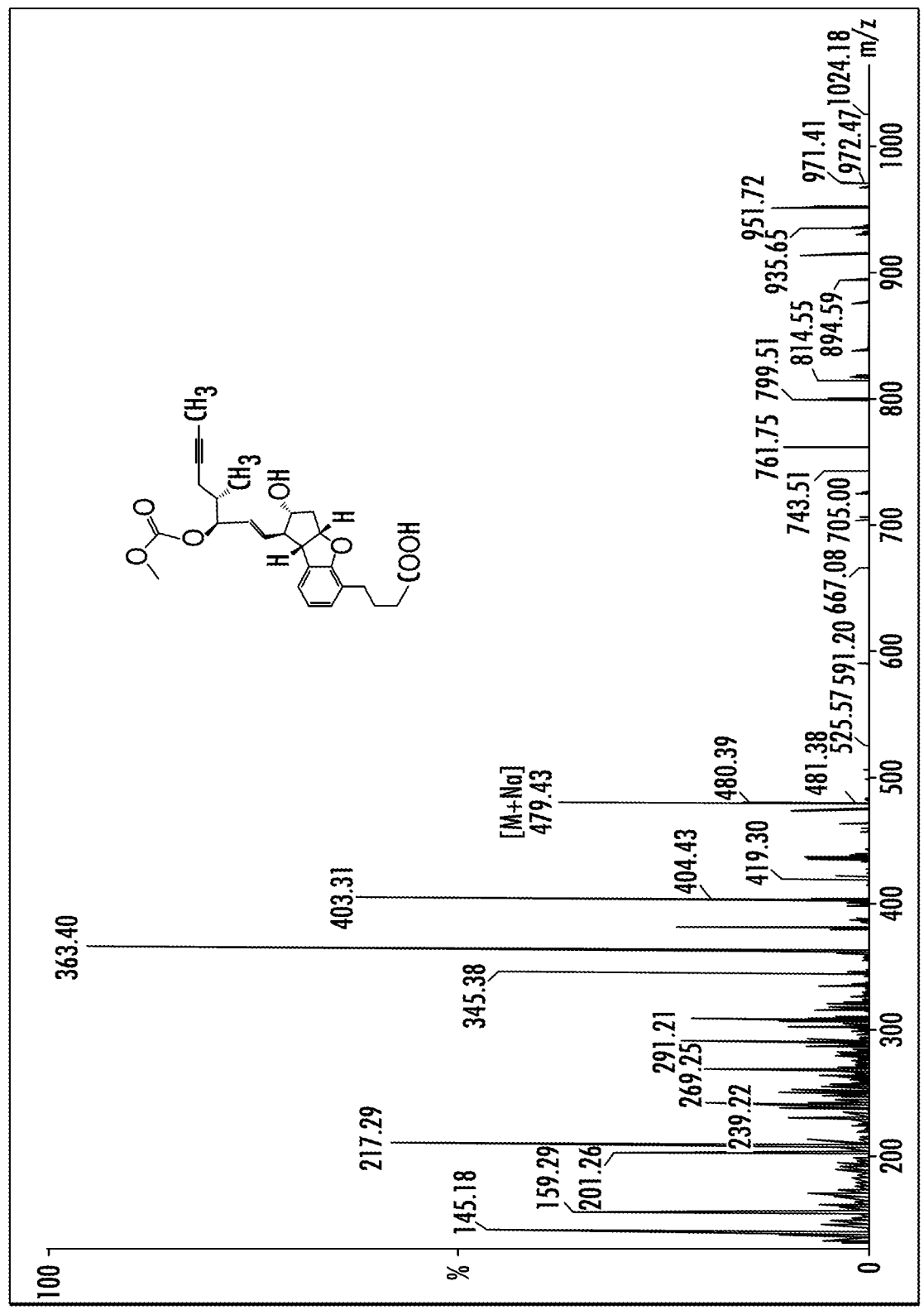
FIG. 13 shows mass spectrum of compound (8).
Figure 14:
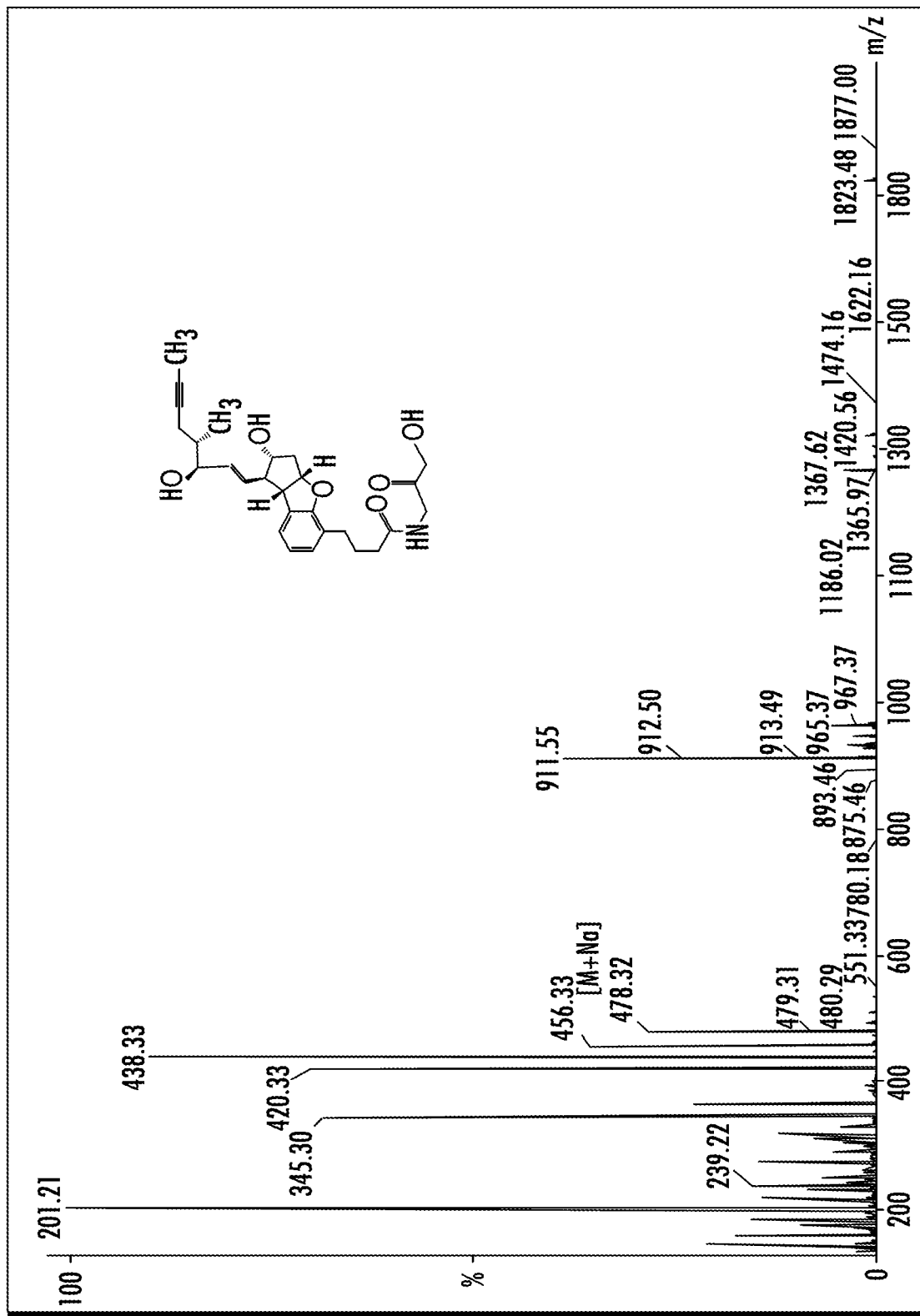
FIG. 14 shows mass spectrum of compound (11).
Figure 15:
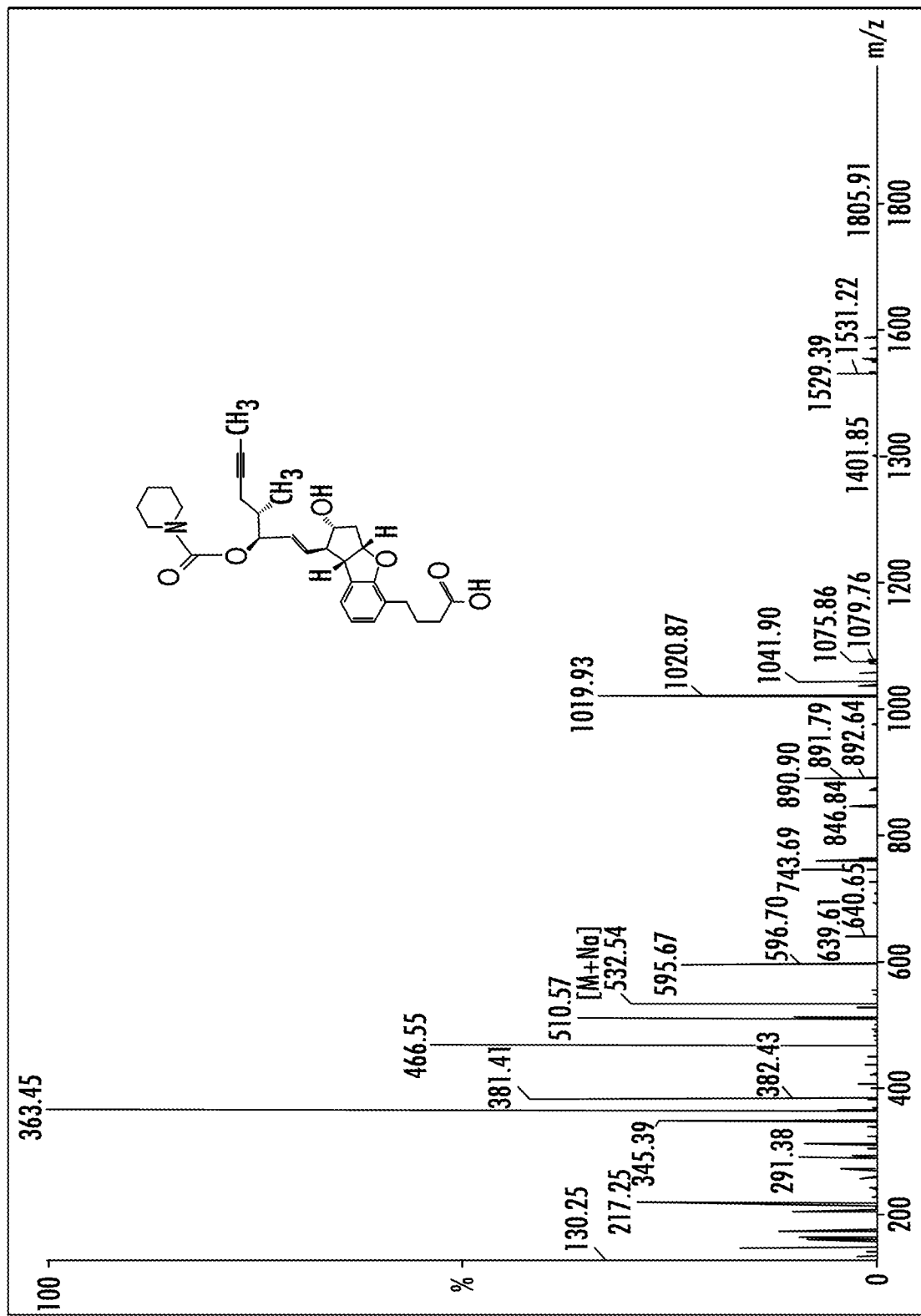
FIG. 15 shows mass spectrum of compound (14).

As used herein, "about" will be understood by persons of ordinary skill in the art and will vary to some extent depending upon the context in which it is used. If there are uses of the term which are not clear to persons of ordinary skill in the art, given the context in which it is used, such as before a numerical designation, e.g., temperature, time, amount, and concentration, including range, indicates approximations which may vary by (+) or (−) 10%, 5% or 1%.

The use of the terms "a" and "an" and "the" and similar references in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The expression "comprising" means "including, but not limited to." Thus, other non-mentioned substances, additives, carriers, or steps may be present.

In general, "substituted" refers to an alkyl, alkenyl, alkynyl, aryl, heteroaryl, heterocyclyl, or ether group, as defined below (e.g., an alkyl group) in which one or more bonds to a hydrogen atom contained therein are replaced by a bond to non-H or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

As used herein, cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

As used herein, alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl" or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, heteroalkyl group include straight and branched chain alkyl groups as defined above and further include 1, 2, 3, 4, 5, or 6 heteroatoms independently selected from oxygen, sulfur, and nitrogen. Thus, heteroalkyl groups include 1 to 12 carbon atoms, 1 to 10 carbons or, in some embodiments, from 1 to 8, or 1, 2, 3, 4, 5, or 6 carbon atoms, or any range therein (e.g., 1-4). Examples of heteroalkyl groups include, but are not limited to, —(CH$_2$CH$_2$O)$_{1-5}$CH$_3$, —(CH$_2$)$_{1-6}$O(CH$_2$)$_{1-6}$ CH$_3$, —(CH$_2$)$_{1-6}$NR$_a$(CH$_2$)$_{1-6}$ CH$_3$, —$(CH_2)_{1-6}S(CH_2)_{1-6}CH_3$, —$(CH_2)_{1-6}O(CH_2)_{1-6}O(CH_2)_{1-6}CH_3$, —$(CH_2)_{1-6}NR_a(CH_2)_{1-6}NR_a(CH_2)_{1-6}CH_3$, —$(CH_2)_{1-6}O(CH_2)_{1-6}O(CH_2)_{1-6}O(CH_2)_{1-6}CH_3$, —$(CH_2)_{1-6}NR_a(CH_2)_{1-6}NR_a(CH_2)_{1-6}NR_a(CH_2)_{1-6}CH_3$, with the total number of carbon atoms in the heteroalkyl group being 1 to 12 and $R^a$ is a H or a substituted or unsubstituted alkyl, alkenyl, aryl or aralkyl group. Other examples of heteroalkyl groups include, but are not limited to, groups having different heteroatoms in a single group. Such examples of heteroalkyl groups include, but are not limited to, —$(CH_2)_{1-6}(CH_2)_{1-6}O(CH_2)_{1-6}$, —$(CH_2)_{1-6}NR_a(CH_2)_{1-6}O(CH_2)_{1-6}$, —$(CH_2)_{1-6}(CH_2)_{1-6}NR_a(CH_2)_{1-6}S(CH_2)_{1-6}$, —$(CH_2)_{1-6}NR_a(CH_2)_{1-6}O(CH_2)_{1-6}S(CH_2)_{1-6}$, with the total number of carbon atoms in the heteroalkyl group being 1 to 12. In some embodiments, heteroalkyl groups include, but are not limited to, polyoxyethylene groups, such as —$(OCH_2CH_2CH_2—)_{1-5}CH_3$, for example, $O(CH_2)_2O(CH_2)_2OCH_3$, —$O(CH_2)_2O(CH_2)_2O(CH_2)_2OCH_3$, —$(CH_2)_2O(CH_2)_2O(CH_2)_2O(CH_2)_2CH_3$.

As used herein, heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) may also be in oxidized form, if chemically possible.

As used herein, heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, imidazolyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) may also be in oxidized form, if chemically possible.

As used herein, the term "halogen" or "halo" as used herein refers to bromine, chlorine, fluorine, or iodine. In some embodiments, the halogen is fluorine. In other embodiments, the halogen is chlorine or bromine. The term "halide" as used herein refers to the anion of a halogen, such as bromide, chloride, fluoride, and iodide. In some embodiments, the halide is chloride or iodide.

As used herein, the terms "alkoxy" refers to a substituted or unsubstituted alkyl group bonded to an oxygen atom. Examples include but are not limited to methoxy and ethoxy. Representative substituted alkoxy groups may be substituted one or more times with substituents such as those listed above, such as methoxymethyl and fluoromethoxy.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, the term treatment excludes prevention or prophylaxis.

An animal, subject or patient for diagnosis or treatment refers to an animal such as a mammal, or a human, ovine, bovine, feline, canine, equine, simian, etc. Non-human animals subject to diagnosis or treatment include, for example, simians, murine, such as, rat, mice, canine, leporid, livestock, sport animals, and pets. In one aspect, the subject is a human. It is to be understood that the terms "subject" and "patient" are interchangeable.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response.

The term "pharmaceutically acceptable" as used herein refers to that which is safe and sufficiently non-toxic for administration to a subject. By way of non-limiting example, some pharmaceutically acceptable salt or ester that are contemplated for use in connection with the present invention include those formed with an inorganic base, organic base, inorganic acid, organic acid, or amino acid (basic or acidic amino acid). Salts of inorganic bases can be, for example, salts of alkali metals such as sodium or potassium; alkaline earth metals such as calcium and magnesium or aluminum; and ammonia. Salts of organic bases can be, for example, salts trimethylamine, triethylamine, pyridine, picoline, ethanolamine, diethanolamine, and triethanolamine. Salts of inorganic acids can be, for example, salts of hydrochloric acid, hydroboric acid, nitric acid, sulfuric acid, and phosphoric acid. Salts of organic acids can be, for example, salts of formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides. Amino acid salts can be, for example, salts of glycine, alanine, arginine, asparagine, aspartic acid, cysteine, glutamine, glutamic acid, histidine, isoleucine, leucine, lysine, methionine, phenylalanine, serine, tryptophan, threonine, tyrosine, valine, citrulline, or ornithine.

As used herein, "protecting group" or "protective group" is used as known in the art and as demonstrated in Greene, *Protective Groups in Organic Synthesis*.

As used herein, "hydroxyl protective group" or "hydroxy protecting group" or "hydroxyl blocking group" refers to the generally understood definition of an alcohol or hydroxy protecting group as defined in T. W. Greene, *Protective Groups in Organic Synthesis*, John Wiley and Sons, 1991 (hereinafter "Greene, *Protective Groups in Organic Synthesis*").

As used herein, "acid protective group" or "acid protecting group" or "carboxylic acid blocking group" refers to the generally understood definition of protection for the carboxylic acid group as defined in T. W. Greene, *Protective Groups in Organic Synthesis*, John Wiley and Sons, 1991 (hereinafter "Greene, *Protective Groups in Organic Synthesis*").

As used herein, "amine protective group" or "amine protecting group" refers to the generally understood definition of protection for the amino group as defined in T. W. Greene, *Protective Groups in Organic Synthesis*, John Wiley and Sons, 1991 (hereinafter "Greene, *Protective Groups in Organic Synthesis*").

As used herein, "an alcohol protecting group" or "alcohol protective group" is a functional group that protects the alcohol group from participating in reactions that are occurring in other parts of the molecule. Suitable alcohol protecting groups are well known to those of ordinary skill in the art and include those found in T. W. Greene, *Protecting Groups in Organic Synthesis*, John Wiley & Sons, Inc. 1981, the entire teachings of which are incorporated herein by reference. Exemplary alcohol protecting groups include, but are not limited to, actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS) ether), tetrahydropyranyl (THP), methyl ether and ethoxyethyl ether (EE). In some embodiments, the terms "hydroxy protecting group" and "alcohol protecting group" are used interchangeably.

As used herein, substantially pure compound or isomer refers to one isomer being 90% of the resulting isomeric mixture, or preferably 95% of the resulting isomeric mixture, or more preferably 98% of the resulting isomeric mixture, or even more preferably 99% of the resulting isomeric mixture, and most preferably above 99% of the resulting isomeric mixture.

Abbreviations: The following abbreviations are used in this disclosure:

CDI: 1,1'-carbonyldiimidazole

DBU: 1,8-diazabicyclo[5.4.0]undec-7-ene;

DCM: dicloromethane;

DCE: dicloroethane;

EDCl/EDC: 1-Ethyl-3-(3-dimethylaminopropyl)carbodiimide;

EtOAc: ethyl acetate;

HCl: hydrogen chloride;

MeOH: methanol;

TBAF: tetrabutylammonium fluoride;

TBDMS: tert-butyl dimethylsilyl;

TEA: triethylamine;

TMSE: trimethylsilyl ether

THF: tetrahydrofuran.

Compounds

Esuberaprost has the following chemical formula:

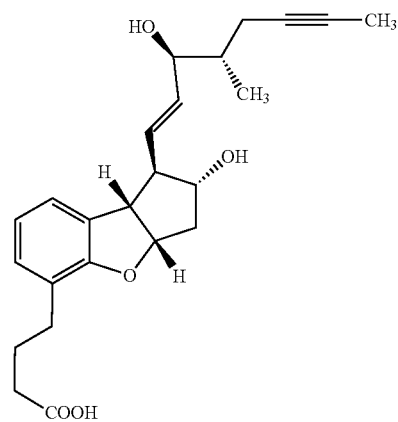 [SMILES: CC#CC[C@H](C)[C@H](O)/C=C/[C@@H]1[C@H]2c3cccc(CCCC(=O)O)c3O[C@H]2C[C@H]1O]

The present inventors have developed novel prodrugs of esuberaprost. The phrase "prodrug(s) of esuberaprost" (also referred to "esuberaprost prodrug(s)" or just "prodrug(s)" depending on context) as used herein refers to any derivative of esuberaprost that converts in whole or in part to esuberaprost in vivo following administration.

In one aspect, the present technology relates to prodrugs of esuberaprost. For example, the prodrug may be a compound having Formula (I), or a diastereomer, enantiomer or pharmaceutically acceptable salt of the compound of Formula (I):

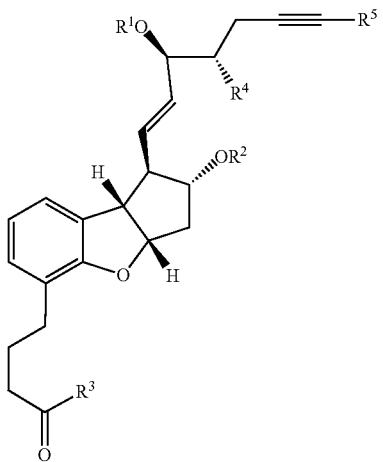

(I)

wherein
$R^1$ and $R^2$ each independently represent H, $C_1$-$C_6$ alkyl, —$CO_2R^6$, —$CONR^6R^7$, —$P(O)(OH)_2$—, —$(CH_2)_2OP(O)(OH)_2$— or a hydroxy protecting group, or wherein $OR^1$ or $OR^2$ forms an ester of an amino acid, or wherein $R^1$ and $R^2$ connected to carbonyl to make a cyclic carbonate group, or wherein $OR^1$ or $OR^2$ together form a phosphate group;

$R^3$ represents $NR^7R^8$, $OR^9$, or $NHSO_2R^{10}$;

$R^4$ represents H or $C_{1-3}$ alkyl;

$R^5$, $R^6$ and $R^7$ each independently represent H or $C_{1-6}$ alkyl, or wherein $R^6$ and $R^7$ together with the nitrogen to which they are attached form a piperidine or a bipiperidine ring;

$R^8$ represents H, optionally substituted $C_1$-$C_6$ alkyl, or

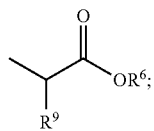

or wherein $R^7$ and $R^8$ are such that $NR^7R^8$ is an amide of an amino acid;

$R^9$ represents H or $C_1$-$C_6$ alkyl, which may be optionally substituted with a terminal hydroxyl or carboxy group; and $R^{10}$ represents H, optionally substituted $C_1$-$C_6$ alkyl, optionally substituted $C_6$-$C_{10}$ aryl, optionally substituted $C_3$-$C_8$ heteroaryl or optionally substituted heterocyclyl;

with a proviso that all of $R^1$, $R^2$ and $R^8$ are not H.

Examples of $C_{1-6}$ alkyl include a linear or branched chain alkyl group such as a methyl, ethyl, n-propyl, isopropyl, n-butyl, isobutyl, sec-butyl, tert-butyl, n-pentyl and n-hexyl. The alkyl group may be substituted with at least one substituent selected from the group consisting of halogen, cyano, nitro, $C_3$-$C_6$ cycloalkyl, $C_6$-$C_{10}$ aryl, $C_3$-$C_8$ heteroaryl, $C_1$-$C_3$ alkoxy, $C_2$-$C_{14}$ disubstituted amino and a $C_2$-$C_{14}$ disubstituted carbamoyl.

Examples of $C_6$-$C_{10}$ aryl include phenyl and naphthyl. Examples of $C_3$-$C_8$ heteroaryl include pyrrolyl, furyl, thienyl, oxazolyl, isoxazolyl, thiazolyl, purine, imidazolyl, pyridyl, pyridazyl, pyrimidyl, benzofuryl, indolyl, quinolyl, and quinazolyl. The heteroaryl group may be substituted with at least one substituent selected from the group consisting of $C_1$-$C_4$ alkyl, benzyl, $C_6$-$C_{10}$ aryl, halogen, $C_1$-$C_3$ alkoxy, nitro, cyano and $C_2$-$C_{14}$ disubstituted amino group.

The heterocyclyl group may be saturated or partially unsaturated 3- to 11-membered heterocyclyl ring containing one to four heteroatoms independently selected from the group consisting of O, N and S. Examples of heterocyclyl group include pyrrolidine, tetrahydrofuran, piperidine, morpholine, piperazine, dioxolane, dioxane and dihydropyranyl. The heterocyclyl group may be substituted with at least one substituent selected from the group consisting of halogen, hydroxy, cyano, nitro, $C_3$-$C_6$ cycloalkyl, $C_6$-$C_{10}$ aryl, $C_3$-$C_8$ heteroaryl, $C_1$-$C_3$ alkoxy, and $C_2$-$C_{14}$ disubstituted amino.

Examples of halogen include F, Cl, Br and I. Examples of $C_3$-$C_6$ cycloalkyl include cylopropyl, cyclopentyl and cyclohexyl. Examples of $C_1$-$C_3$ alkoxy include methoxy, ethoxy and propoxy. Examples of $C_1$-$C_3$ alkylthio include methylthio, ethylthio and propylthio. Examples of $C_6$-$C_{14}$ arylthio include phenylthio and naphthylthio. Examples of $C_2$-$C_{14}$ disubstituted amino include dimethylamino, diethylamino, diisopropylamino, diphenylamino, dibenzylamino and methylbenzylamino. Examples of the $C_2$-$C_{14}$ disubstituted carbamoyl include dimethylcarbamoyl, diethylcarbamoyl, dibenzylcarbamoyl and benzylmethylcarbamoyl.

Amino acid(s) may include a D-isomer amino acid or an L-isomer amino acid. In certain embodiments, an amino acid may be a naturally occurring amino acid. Yet, in some embodiments, an amino acid may be an artificial amino acid. Examples of amino acids include, but not limited to, carbamic acid, glycine, alanine, valine, leucine, isoleucine, methionine, proline, phenylalanine, tryptophan, serine, threonine, asparagine, glutamine, tyrosine, cysteine, lysine, arginine, histidine, asparatice acid, glutamic acid.

In some embodiments, $R^3$ may be OH. In such a case, in certain embodiments, each of $R^1$ and $R^2$ may be each independently selected from the group consisting of H, —$CO_2R^6$, —$CONR^6R^7$, —$P(O)(OH)_2$, —$(CH_2)_2OP(O)(OH)_2$, —$C(O)$-piperadine, and —$C(O)$-bipiperadine. $R^1$ and $R^2$ may be the same or different. For example one of $R^1$ and $R^2$ may be H and the other may be selected from the group consisting of H, —$CO_2R^6$, —$CONR^6R^7$, —$P(O)(OH)_2$, —$(CH_2)_2OP(O)(OH)_2$, —$C(O)$-piperadine, and —$C(O)$-bipiperadine. In some embodiments, $OR^1$ or $OR^2$ forms an ester of an amino acid. In some embodiments, $OR^1$ or $OR^2$ together form a phosphate group. In some embodiments, $R^1$ and $R^2$ connected to carbonyl to make a cyclic carbonate group.

In some embodiments, when $R^3$ is OH, at least one $R^1$ and $R^2$ may be —$CO_2R^6$. In such a case, $R^6$ may be selected from H and $C_{1-6}$ alkyl, such as methyl. In certain embodiments, both of $R^1$ and $R^2$ may be —$CO_2R^6$. In certain other embodiments, one of $R^1$ and $R^2$ may be —$CO_2R^6$ and the other may be H. In such a case, $R^6$ may be methyl.

In some embodiments, when $R^3$ is OH, $R^1$ and $R^2$ may be —$CONR^6R^7$. In such a case, each of $R^6$ and $R^7$ may be independently selected from H and $C_1$-4 alkyl, such as methyl. In some embodiments, $R^6$ and $R^7$ may be the same. For example, in some embodiments, both of $R^6$ and $R^7$ may be H or both of $R^6$ and $R^7$ may be methyl. Yet in some embodiments, $R^6$ and $R^7$ may be different. For example, one of $R^6$ and $R^7$ may be H, while the other may be methyl. In certain embodiments, $R^6$ and $R^7$ together with the nitrogen to which they are attached form a piperidine ring. In certain other embodiments, $R^6$ and $R^7$ together with the nitrogen to which they are attached form a bipiperidine ring.

In some embodiments, when $R^3$ is OH, at least one $R^1$ and $R^2$ may be —$(CH_2)_2OP(O)(OH)_2$—. In certain embodiments, both of $R^1$ and $R^2$ may be —$(CH_2)_2OP(O)(OH)_2$—. In certain other embodiments, one of $R^1$ and $R^2$ may be —$(CH_2)_2OP(O)(OH)_2$— and the other may be H.

In some embodiments, when $R^3$ is OH, at least one $R^1$ and $R^2$ may be phosphate (—$P(O)(OH)_2$—). In certain embodiments, both of $R^1$ and $R^2$ may be phosphate. In certain other embodiments, one of $R^1$ and $R^2$ may be phosphate and the other may be H.

In some embodiments, when $R^3$ is OH, $R^1$ and $R^2$ are connected to carbonyl to make a cyclic carbonate group. In certain other embodiments, when $R^3$ is OH, $OR^1$ or $OR^2$ together form a phosphate group.

In some embodiments, when $R^3$ is OH, at least one $R^1$ and $R^2$ may be an amino acid selected from the group consisting of glycine, alanine, arginine, asparagine, aspartic acid, cysteine, glutamine, glutamic acid, histidine, isoleucine, leucine, lysine, methionine, phenylalanine, serine, tryptophan, threonine, tyrosine, valine, citrulline, and ornithine. In certain embodiments, both of $R^1$ and $R^2$ may be an amino acid. In certain other embodiments, one of $R^1$ and $R^2$ may be an amino acid and the other may be H.

In some embodiments, when $R^1$ and $R^2$ each independently represent H or hydroxyl protecting group. In such case, in certain embodiments, $R^3$ represents $NR^7R^8$, $OR^9$, or $NHSO_2R^{10}$.

In some embodiments, when $R^1$ and $R^2$ are H or hydroxy protecting group, $R^3$ is $NR^7R^8$. $R^7$ may be H or $C_1$-$C_6$ alkyl. $R_8$ may be

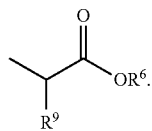

$R^6$ may be H or $C_1$-$C_6$ alkyl and $R^9$ may be H or $C_1$-$C_6$ alkyl, which may be optionally substituted with a terminal hydroxy or carboxy group. In certain embodiments, $R^7$ and $R^8$ are such that $NR^7R^8$ may form an amide of an amino acid.

In certain embodiments. $R^7$ may be H. In such case, in some embodiments, $R^8$ may be

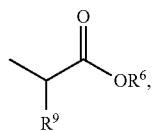

where $R^9$ may be H and $R^6$ may be methyl.

In some embodiments, when $R^1$ and $R^2$ are H or hydroxyl protecting group, $R^3$ is $NHSO_2R^{10}$. In such case, in some embodiments, $R^{10}$ may be selected from the group consisting of optionally substituted $C_1$-$C_6$ alkyl, optionally substituted $C_6$-$C_{10}$ aryl, optionally substituted $C_3$-$C_8$ heteroaryl or optionally substituted heterocyclyl group.

In some embodiments, when $R^1$ and $R^2$ are H and $R^3$ is $NHSO_2R^{10}$, $R^{10}$ may be $C_{1-4}$ alkyl, such as methyl or ethyl. In other embodiments, when $R^1$ and $R^2$ are H and $R^3$ is $NHSO_2R^{10}$, $R^{10}$ may be $C_{6-10}$ aryl, such as phenyl or naphthyl. In certain cases, $R^{10}$ may be $C_{6-10}$ aryl which may be substituted with substituents as defined above.

In some embodiments, when $R^1$ and $R^2$ are H and $R^3$ is an amino acid selected from the group consisting of glycine, alanine, arginine, asparagine, aspartic acid, cysteine, glutamine, glutamic acid, histidine, isoleucine, leucine, lysine, methionine, phenylalanine, serine, tryptophan, threonine, tyrosine, valine, citrulline, and ornithine.

In some embodiments, when $R^2$ is H and $R^3$ is OH, $R^1$ is selected from the group consisting of H, $CO_2CH_3$, $CONHCH_3$, $(CH_2)_2OP(O)(OH)_2$, $P(O)(OH)_2$,

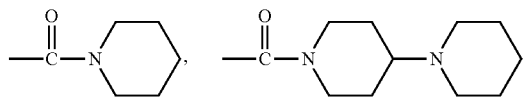

and an amino acid.

In some embodiments, when $R^1$ is H and $R^3$ is OH, $R^2$ is selected from the group consisting of H, $CO_2CH_3$, $CONHCH_3$, $(CH_2)_2OP(O)(OH)_2$, $P(O)(OH)_2$,

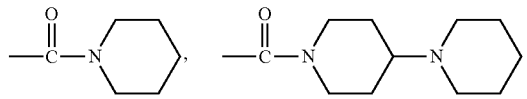

and an amino acid.

In some embodiments, the prodrug may be a compound having one of the following formulas:

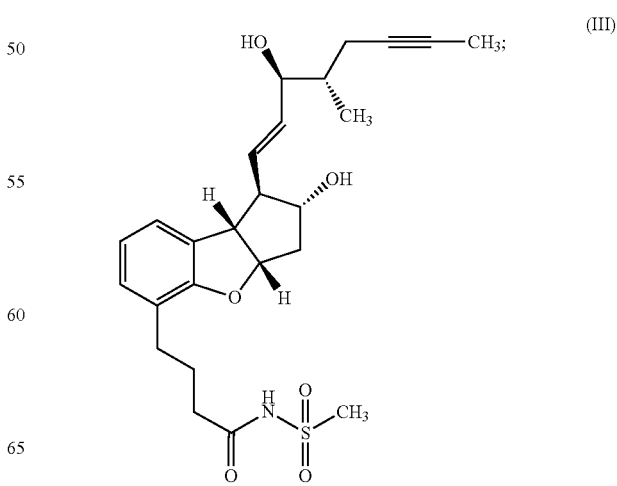

(III)

(VI)

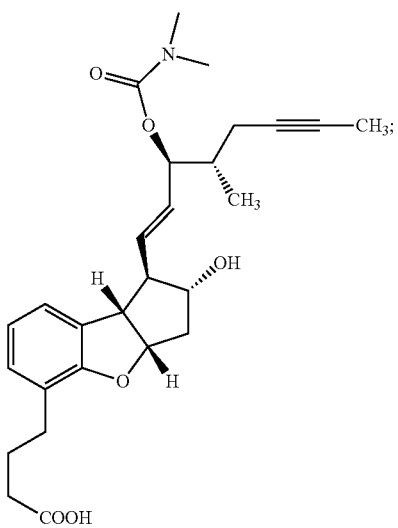

(VIII)

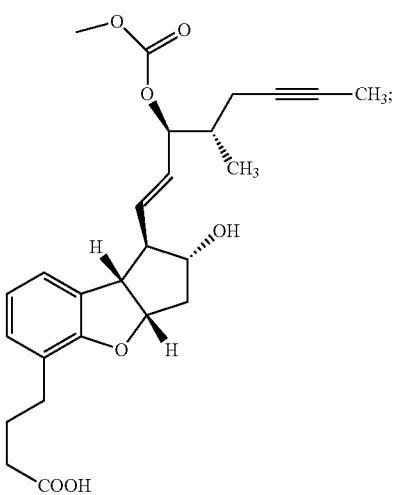

(XI)

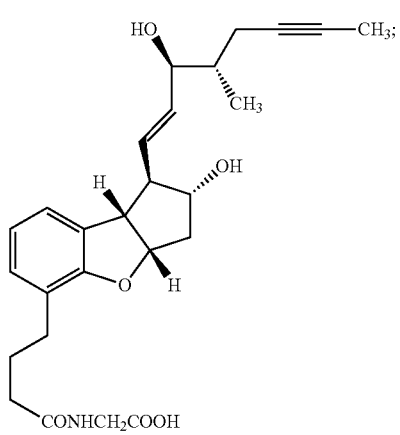

(XIV)

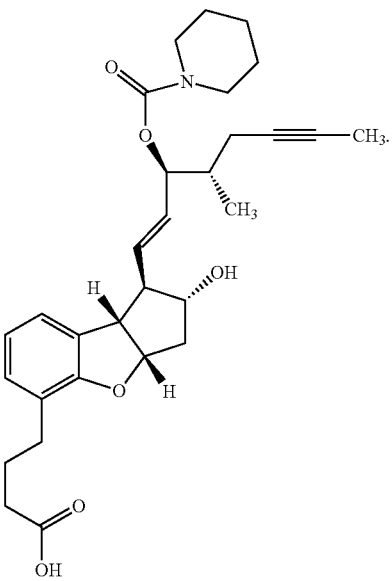

In some embodiments, the prodrug can be an esuberaprost derivative with one or more hydroxyl groups or the carboxylic acid group of the esuberaprost structure modified, but which can be converted in vivo into active esuberaprost following administration and subsequent diffusion into the blood. In some embodiments, the prodrug of esuberaprost is completely or substantially converted in vivo to esuberaprost outside the subcutaneous space, such as in the bloodstream. Preferred prodrugs include the compounds of Formula I above. Other preferred prodrugs of esuberaprost include amide, carbonate, or carbamate esters of esuberaprost. These prodrugs may have one or more advantages compared to esuberaprost or a salt thereof. For example, some of these prodrugs may have improved stability or greater tolerance in at least some patient populations.

In some embodiments, the prodrug of esuberaprost has greater than 50%, 75%, 85%, 90%, 95%, or 98% conversion to esuberaprost in vivo following administration. In some embodiments, this conversion takes place in 15 minutes, 30 minutes, 45 minutes, 1 hour, 2 hour, or 3 hours following administration. Prodrugs of esuberaprost include pharmaceutically acceptable salts of such prodrugs.

Preferably, the prodrugs of esuberaprost are stable during storage, for example, by not hydrolyzing into esuberaprost spontaneously in a solution before administering or during initial injection and at the site of injection. Preferably, the prodrug formulations of the present invention are free of esuberaprost or substantially free of esuberaprost in free acid form. In some embodiments, less than 10%, 5%, 2%, 1%, or 0.1% of the prodrug of esuberaprost converts to esuberaprost during a defined storage period. In some embodiments, that defined storage period can be 1, 2, 3, 6, or 12 months.

Pharmaceutical Compositions

Esuberaprost prodrugs of the present technology may be provided in a form of a pharmaceutical composition, which may also comprise a pharmaceutically acceptable carrier, excipient, binder, diluent or the like. Such pharmaceutical composition may be manufactured by methods known in the art such as granulating, mixing, dissolving, encapsulating, lyophilizing, emulsifying or levigating processes, among others. The composition may be in the form of, for example, granules, powders, tablets, capsules, syrup, suppositories, injections, emulsions, elixirs, suspensions and solutions. The composition may be formulated for a number of different administration routes, such as, for oral administration, transmucosal administration, rectal administration, transdermal or subcutaneous administration, as well as intrathecal, intravenous, intramuscular, intraperitoneal, intranasal, intraocular or intraventricular injection. The esuberaprost prodrug may be administered by any of the above routes, for example in a local rather than a systemic administration, including as an injection or as a sustained release formulation.

In one embodiment, the pharmaceutical composition can compromise a prodrug of esuberaprost and a carrier, such as sterile water. In some embodiments, the prodrug of esuberaprost is formulated for subcutaneous administration, and such formulation may or may not include m-cresol or another preservative.

For oral, buccal, and sublingual administration, powders, suspensions, granules, tablets, pills, capsules, gelcaps, and caplets may be acceptable as solid dosage forms. These can be prepared, for example, by mixing one or more esuberaprost prodrugs, or pharmaceutically acceptable salts thereof, with at least one additive or excipient such as a starch or other additive. Suitable additives or excipients may be sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms may contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers. Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

An esuberaprost prodrug may be formulated in a formulation suitable for parenteral administration that may comprise sterile aqueous preparations of an esuberaprost prodrug, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood.

In some embodiments, a formulation of an esuberaprost prodrug for parenteral administration, such as intravenous infusion or subcutaneous infusion (including continuous subcutaneous infusion), may be prepared by admixing the prodrug with a vehicle, such as a buffer. In certain embodiments, the vehicle may be a phosphate containing vehicle, i.e. at least one phosphate salt, which may be for example, dibasic phosphate, such as sodium dibasic phosphate or potassium dibasic phosphate, or tribasic phosphate, such as sodium tribasic phosphate or potassium phosphate. In certain embodiments, the vehicle may also contain a halogen salt, such as a chloride salt, which may be, for example, sodium chloride or potassium chloride. The halogen salt, such as sodium chloride may be used to adjust tonicity of the vehicle. In certain embodiments, it may be preferred that a phosphate and a halogen salt have the same cation. For example, when a phosphate is sodium phosphate, such as sodium tribasic phosphate or sodium tribasic phosphate, a halogen salt may a sodium halogen salt such as sodium chloride. Similarly, when a phosphate is potassium phosphate, such as potassium tribasic phosphate or potassium tribasic phosphate, a halogen salt may a potassium halogen salt such as potassium chloride. A solvent in the vehicle may contain water. In certain embodiments, water may be the only solvent in the vehicle. Yet in certain embodiments, the vehicle may contain one or more additional solvent in addition to water. In some embodiments, an additional solvent may be a preservative, such as m-cresol.

Preferably, the vehicle is isotonic with blood of a patient, such as a human being. The term isotonic may mean that the osmolarity and ion concentrations of the vehicle match those of the patient, such as human being. Non-limiting example of vehicles include phosphate-buffered saline, which is a water based salt solution containing disodium hydrogen phosphate, sodium chloride and, in some formulations, potassium chloride and potassium dihydrogen phosphate. Other examples may include a vehicle containing 20 mM disbasic sodium phosphate with 125 mM sodium chloride and a vehicle containing 15 mM sodium phosphate tribasic, 125 mM sodium chloride and 0.3% w/w m-cresol.

In certain embodiments, an esuberaprost prodrug may be administered subcutaneously. In some embodiments, the subcutaneous administration may be continuous subcutaneous infusion, such as continuous subcutaneous infusion by an infusion pump, which is preferably portable or implantable.

Therapeutic Methods

The esuberaprost prodrugs may be used for one or more of the same purposes for which esuberaprost is known to be useful, such as for treating a condition, for which esuberaprost is known to be effective. For example, the esuberaprost prodrugs may be used for administering to a subject in need thereof, such as a human being, for treating a disease or disorder, which may be treated with esuberaprost, such as pulmonary hypertension (including primary and secondary pulmonary hypertension and pulmonary arterial hypertension), peripheral vascular disease, severe intermittent claudication, critical limb ischemia, ischemic lesions, asthma, pulmonary fibrosis, diabetic neuropathic foot ulcers, interstitial lung disease. For therapeutic purposes, such as treating pulmonary hypertension, an esuberaprost prodrug may be administered to a subject, such a human being, in a therapeutically effective amount, which may be an amount of the esuberaprost prodrug, which is sufficient to ameliorate one or more symptoms of a disease or disorder, which may be treated with esuberaprost, such as pulmonary hypertension.

Accordingly, provided herein is a method of treating a disease or condition in a patient in need thereof comprising administering to the patient an effective amount of a prodrug of esuberaprost. In at least one embodiment, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma. In at least one embodiment, provided herein is a method of treating pulmonary hypertension comprising, administering subcutaneously to a patient suffering from pulmonary hypertension an effective amount of a prodrug of esuberaprost. In at least one embodiment, provided herein is a method of treating vascular disease comprising, administering subcutaneously to a patient suffering from vascular disease an effective amount of a prodrug of esuberaprost. In some embodiments, provided herein are methods of treating one or more of pulmonary hypertension and vascular disease comprising, administering subcutaneously to a patient suffering from vascular disease an effective amount of a compound of Formula (I).

Methods of Preparation

In one aspect, processes are providing for preparing prostacyclin derivatives. Such derivatives may in some embodiments, include prodrugs of esuberaprost. The processes also include the preparation of a number of intermediate compounds useful in the preparation of prostacyclin derivatives. In one aspect, a process is provided to produce a pharmaceutical compound represented by the general Formula (I), Formula (III), Formula (VI), Formula (VIII), Formula (XI) or Formula (XIV). In some embodiments, a process is provided to produce a pharmaceutical compound represented by the general Formula (I), Formula (III), Formula (VI), Formula (VIII), Formula (XI) or Formula (XIV) in a substantially isomerically pure form. The process is completed in fewer steps than the known synthetic methods, and may be conducted to prepare commercially useful quantities. In another aspect, synthetic methods are provided for producing prodrugs of esuberaprost, which are stereoselective, efficient, scalable and economical. In another aspect, substantially isomerically pure compounds and intermediates are produced by the above processes.

In one embodiment, the present technology relates to a new process for the preparation of esuberaprost prodrugs. The process is a much more efficient, commercially viable process to manufacture the target compounds. In other embodiments, novel synthetic intermediate compounds useful for the synthesis of esuberaprost prodrugs are provided.

In one embodiment, the present technology provides a process for the preparation of a compound of Formula (III):

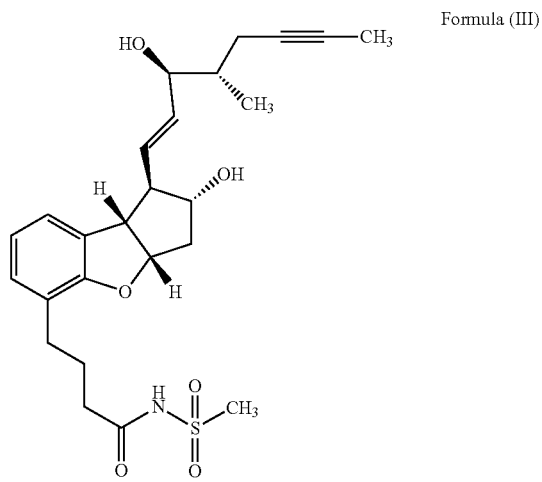 [SMILES: CC#CC[C@H](C)[C@H](O)/C=C/[C@@H]1[C@H]2c3cccc(CCCC(=O)NS(C)(=O)=O)c3O[C@H]2C[C@H]1O]

Formula (III)

comprising:
(a) reacting a compound of Formula (II)

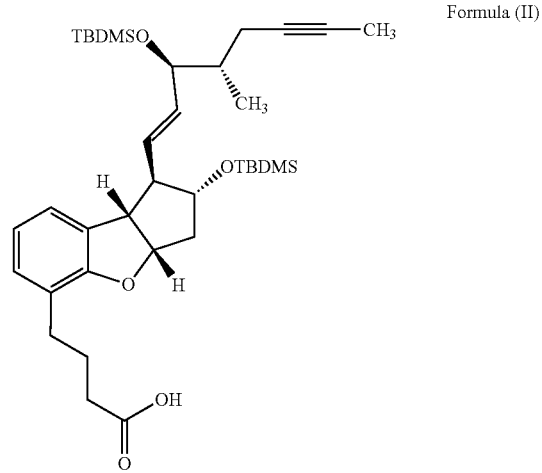 [SMILES: CC#CC[C@H](C)[C@@H](/C=C/[C@@H]1[C@H]2c3cccc(CCCC(=O)O)c3O[C@H]2C[C@H]1O[Si](C)(C)C(C)(C)C)O[Si](C)(C)C(C)(C)C]

Formula (II)

with methanesulfonic acid, optionally in the presence of at least one carboxyl-activating agent, optionally in the presence of at least one suitable coupling agent, to form a compound of Formula (II')

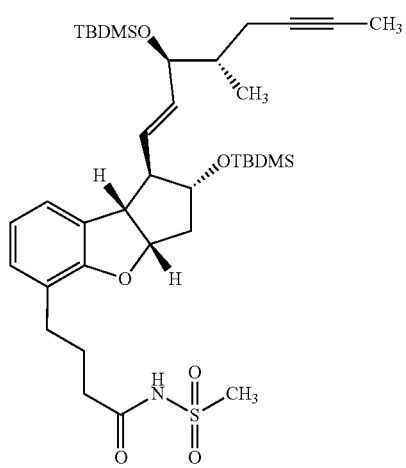

(b) deprotecting the product of Formula (II') of step (a) in acidic condition to form the compound of Formula (III).

In one embodiment, the present technology provides a process for the preparation of a compound of Formula (VI):

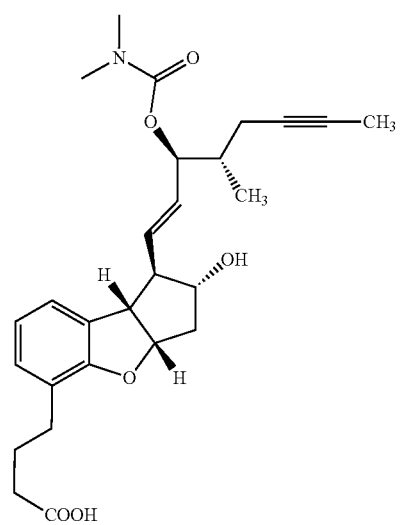

comprising:

(a) reacting a compound of Formula (IV)

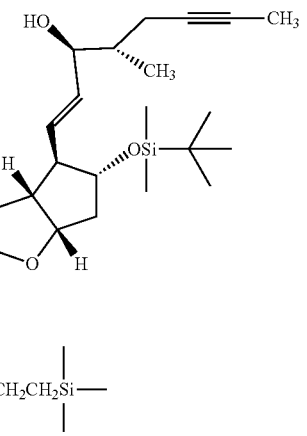

with 4-nitrophenyl chloroformate, optionally in the presence of excess of at least one amine base to form a compound of Formula (V);

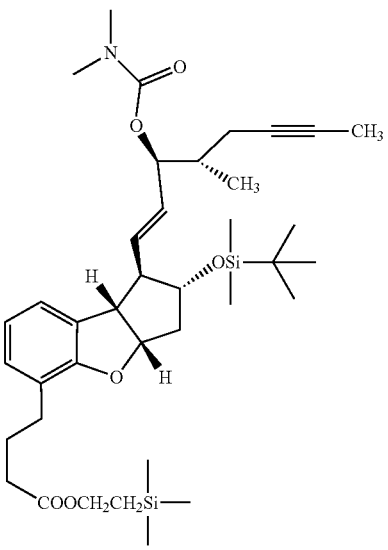

(b) desilylating the compound of Formula (V) of step (a) to form the compound of Formula (VI).

In one embodiment, the present technology provides a process for the preparation of a compound of Formula (VIII):

Formula (VIII)

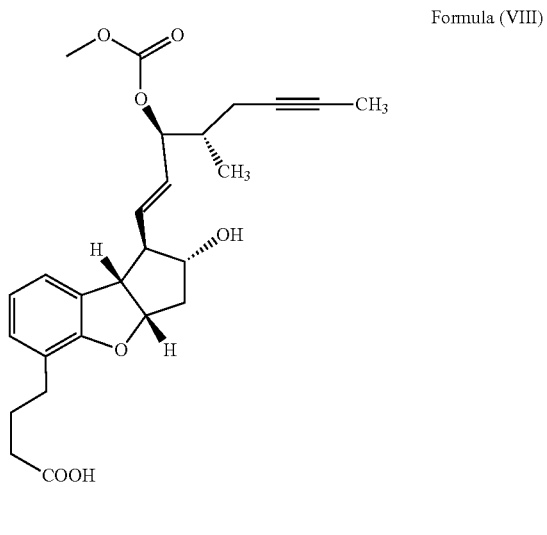 [SMILES: CC#CC[C@H](C)[C@@H](/C=C/[C@@H]1[C@H]2c3cccc(CCCC(=O)O)c3O[C@H]2C[C@H]1O)OC(=O)OC]

Formula (VII)

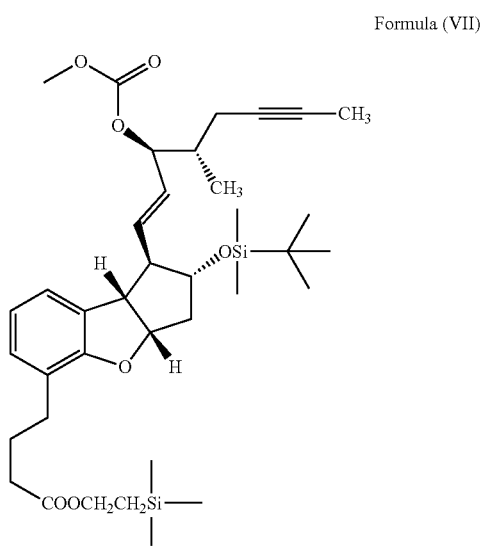

comprising:
(a) reacting a compound of Formula (IV)

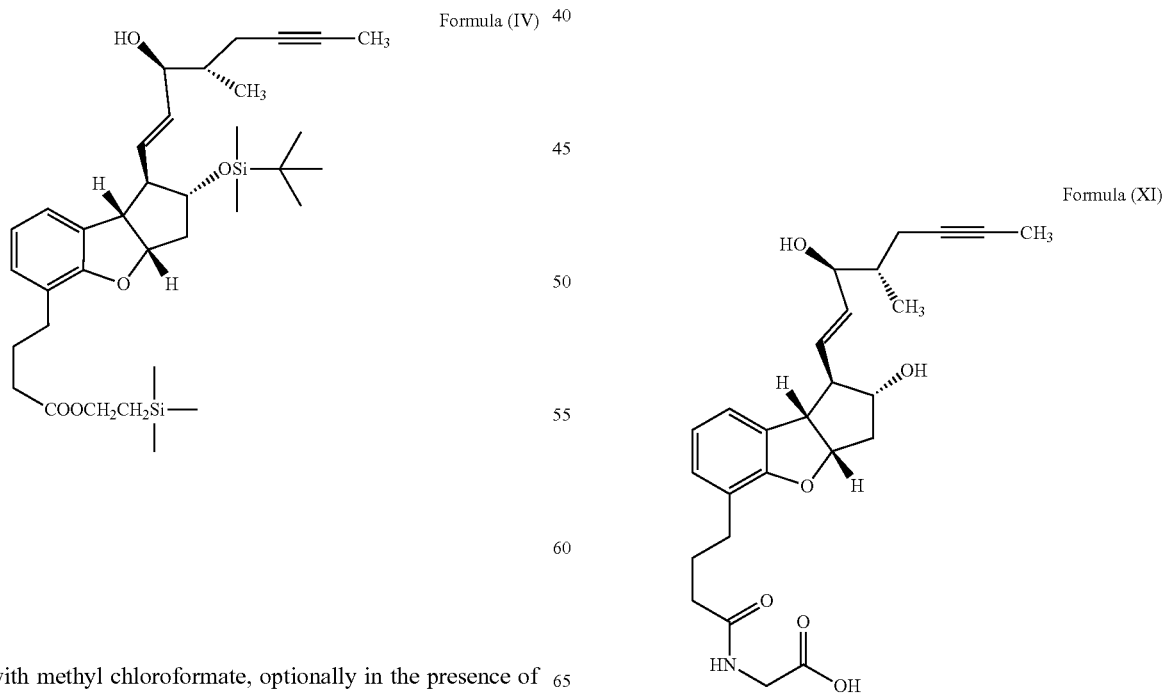

with methyl chloroformate, optionally in the presence of at least one amine base to form a compound of Formula (VII);

(b) desilylating the compound of Formula (VII) of step (a) to form the compound of Formula (VIII).

In one embodiment, the present technology provides a process for the preparation of a compound of Formula (XI):

comprising:
(a) reacting a compound of Formula (IX)

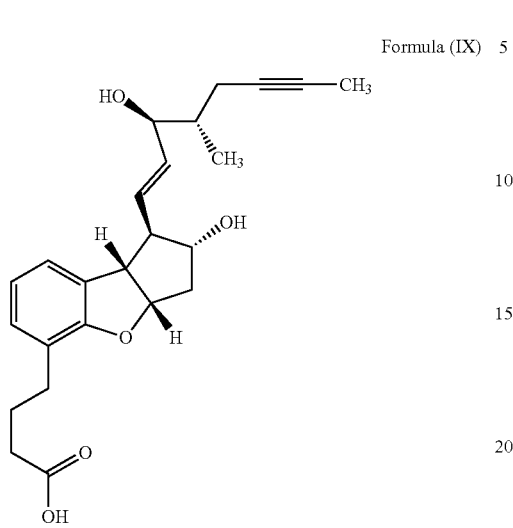

Formula (IX)

with glycine methyl ester hydrochloride, optionally in the presence of at least one carboxyl-activating agent, optionally in the presence of at least one amine base to form a compound of Formula (X);

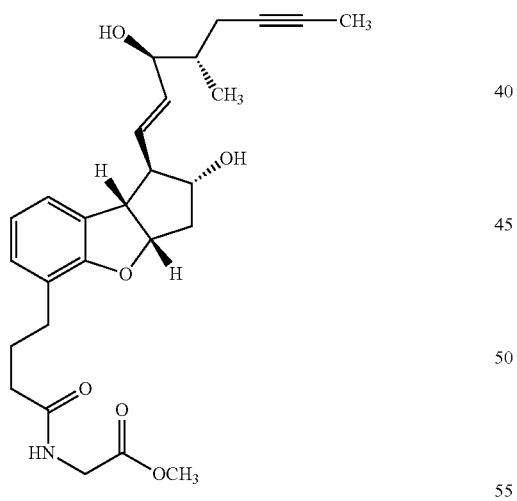

Formula (X)

(b) hydrolyzing the ester of Formula (X) of step (a) to form the compound of Formula (XI).

In one embodiment, the present technology provides a process for the preparation of a compound of Formula (XIV):

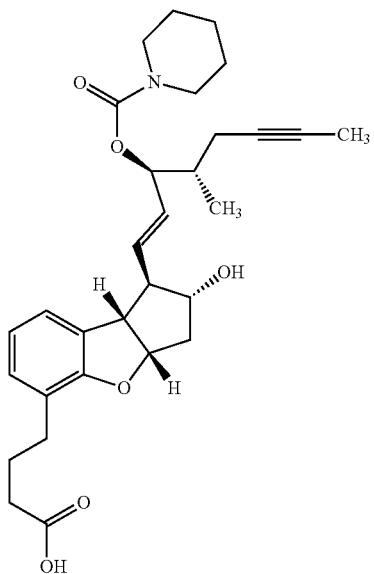

Formula (XIV)

comprising:
(a) reacting a compound of Formula (IV)

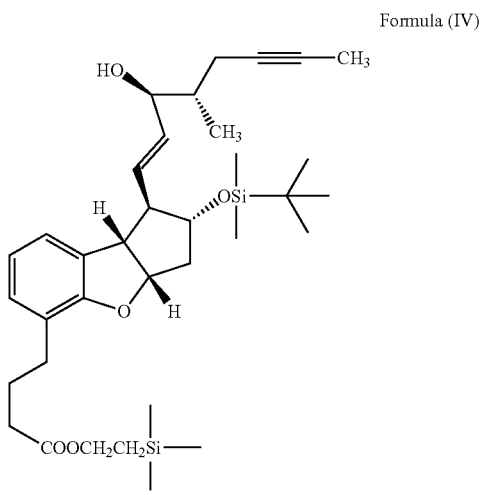

Formula (IV)

with carbonyldiimidazole to form a compound of Formula (XII);

Formula (XII)

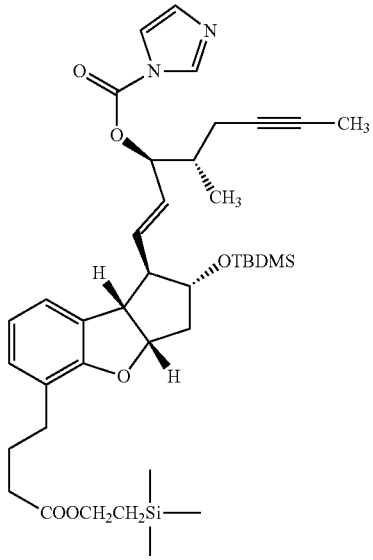

(b) reacting a compound of Formula (XII) with piperidine to form a compound of Formula (XIII);

Formula (XIII)

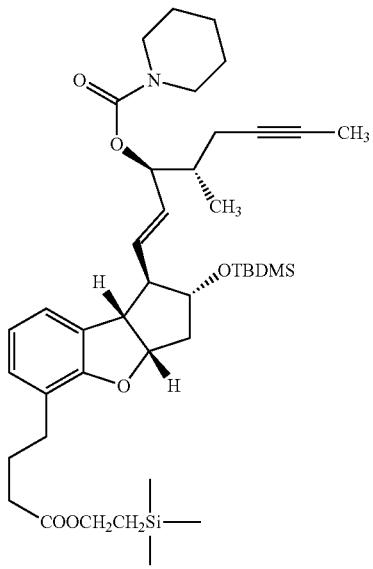

(c) desilylating the compound of Formula (XIII) of step (b) to form the compound of Formula (XIV).

As noted above, the reactions in the process of preparation of esuberaprost prodrugs may be conducted in the presence of suitable carboxyl-activating agents, coupling agents, deprotecting agents, desilylating agents, hydrolyzing agents, acids, bases and solvents. Suitable carboxyl-activating agents include, but are not limited to 1,1'-carbonyldiimidazole (CDI), 1-ethyl-3-(3'-dimethylaminopropyl)carbodiimide hydrochloride (EDCl), 1,3-dicyclohexylcarbodiimide (DCC), benzotriazol-1-yl-oxy-tris(dimethylamino)phosphonium hexafluorophosphate (BOP), and 1,3-Diisopropylcarbodiimide (DICD). Suitable coupling agents include, but are not limited to 1,8-diazabicyclo[5.4.0]undec-7-ene (DBU) and tetramethyluronium hexafluorophosphate (HBTU). Suitable bases include for example, amine bases such as pyridine, N,N,N'N'-tetramethylethylenediamine (TMEDA), dimethylamine (DMA), diethylamine (DEA) and trimethylamine (TEA). Suitable acids include for example, acetic acid, hydrochloric acid and sulfuric acid.

Suitable hydrolyzing agents for removal of the carboxylic acid protective group include, but are not limited to lithium hydroxide, barium hydroxide, sodium hydroxide, potassium hydroxide, calcium hydroxide, ammonium hydroxide, sodium carbonate, potassium carbonate, trimethyltin hydroxide, tributyltin hydroxide, palladium-carbon in presence of hydrogen under basic conditions, and the like, and combinations thereof. In some embodiments, the hydrolyzing agent is trimethyltin hydroxide.

Hydroxy protecting groups can be removed by acid or base catalysed hydrolysis or catalytic hydrogenolysis. For example, tetrahydropyarnyl (THP) ether protecting group may be removed, for example, by acid hydrolysis, silyl ethers may require hydrogen fluoride or tetrabutylammonium fluoride to be cleaved and benzyl ether protecting group may be removed, for example, by hydrogenolysis.

The deprotection reaction of t-butyldimethylsilyl group (TBDMS) and/or trimehtyl silyl ester group (TMSE) can be conducted under relatively mild conditions using acids such as hydrochloric acid, optionally with a solvent such as methanol or ethanol; or fluoride ions, in the form of inorganic salts such as KF, $LiBF_4$ or $NH_4F$, or an organic salt such as tetrabutylammonium fluoride (TBAF), optionally with a solvent such as THF. In at least one embodiment, the deprotection is conducted in the presence of HCl in methanol. In at least one embodiment, the deprotection (e.g., desilylation) is conducted in the presence of TBAF in THF.

Suitable solvents used in the include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane (DCM), ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran (THF), dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof. In some embodiments, the process is conducted in one or more solvents selected from the group consisting of tetrahydrofuran, methanol, dichloromethane, dichloroethane, and water. In some embodiments, the organic solvents such as DCM, DCE, THF and methanol are anhydrous. In at least one embodiment, the solvent is methanol. In at least one embodiment, the solvent is THF. In at least one embodiment, the solvent is DCM.

Esuberaprost prodrugs may be prepared according to methods described in the synthetic schemes below.

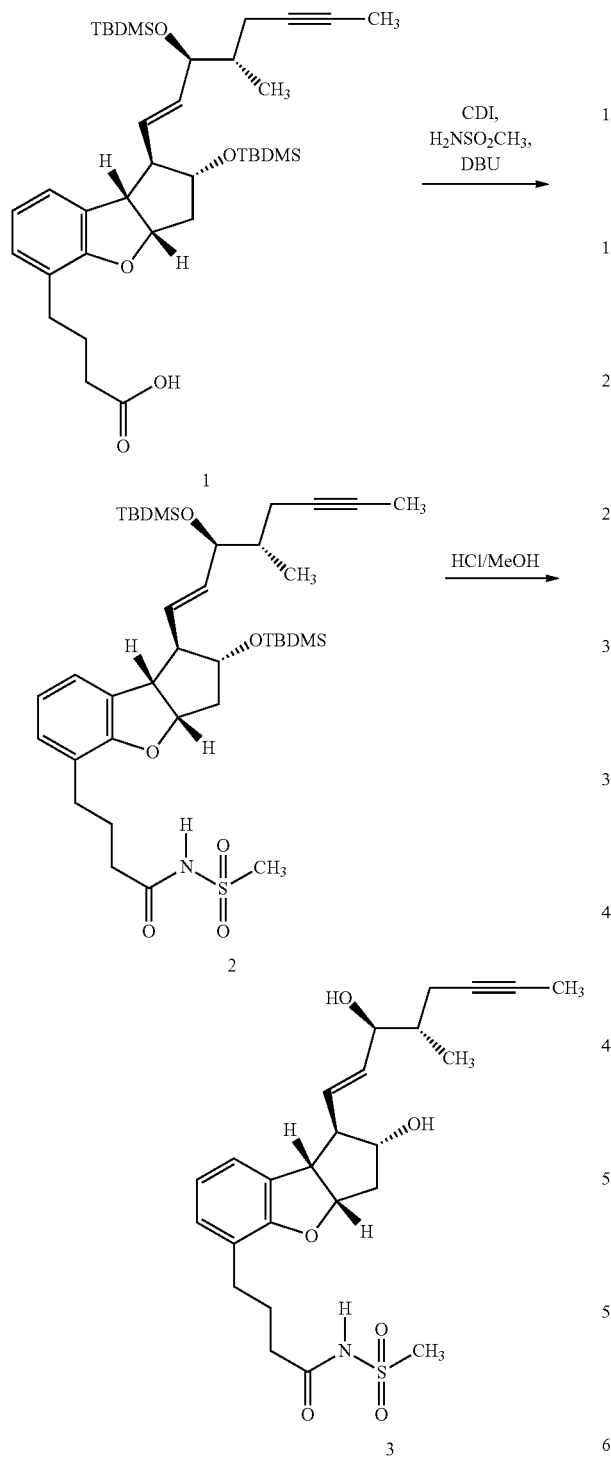

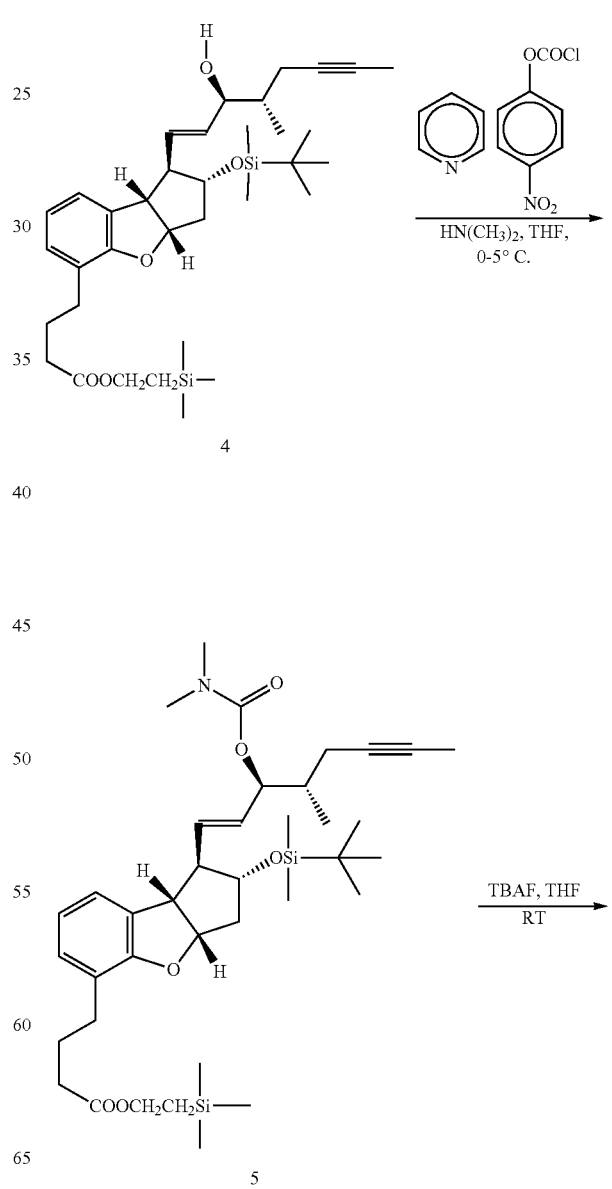

Scheme 1 illustrates synthesis of methanesulfonamide Prodrug 3 (III). This synthesis may start with di-TBDMS protected esuberaprost reacted with $NH_2SO_2CH_3$ to form a protected sulfonamide compound, which can be deprotected to provide the methanesulfonamide Prodrug 3 (III). As shown in Scheme 1, esuberaprost methanesulfonamide (3) was synthesized from di-TBDMS esuberaprost (1). The starting di-TBDMS esuberaprost (1) was prepared from pure esuberaprost in three steps. The activation of acid (1) with CDI followed by reaction with methanesulfonamide in the presence of DBU gave di-TBDMS esuberparost methanesulfonamide (2) and was purified by silica gel column chromatography. The deprotection of TBDMS from sulfonamide (2) using hydrogen chloride in methanol afforded the desired esuberaprost methanesulfonamide (3) after chromatography. This prodrug (3) was characterized by spectral data (IR, $^1$H NMR, $^{13}$C NMR and MS).

31
-continued

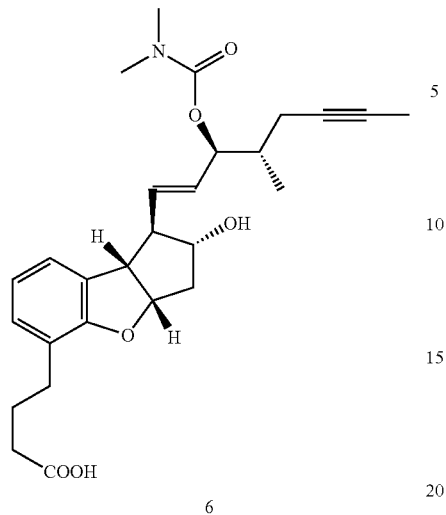

6

32
-continued

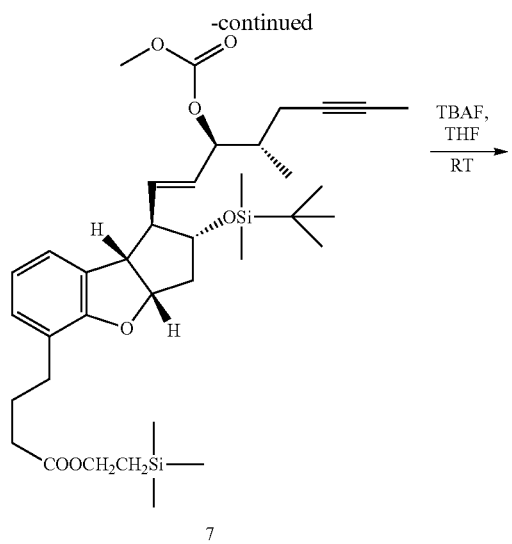

7

TBAF,
THF
———→
RT

As shown in Scheme 2, esuberaprost side chain N,N-dimethyl carbamate (6) was synthesized from TBDMS esuberaprost TMSE ester (4). The TMSE ester (4) was prepared from mono-TBDMS protected esuberaprost acid. The ester (4) was treated with 4-nitrophenyl chloroformate to give 4-nitrophenyl carbonate. The carbonate, without isolation, was treated with dimethylamine in tetrahydrofuran to afford protected dimethyl carbamate (5) after chromatography. The desilylation of compound (5) with tetrabutylammonium fluoride (TBAF) in tetrahydrofuran gave esuberaprost N,N-dimethyl carbamate (6). This prodrug (6) was characterized by spectral data (IR, $^1$H-NMR, $^{13}$C NMR and MS).

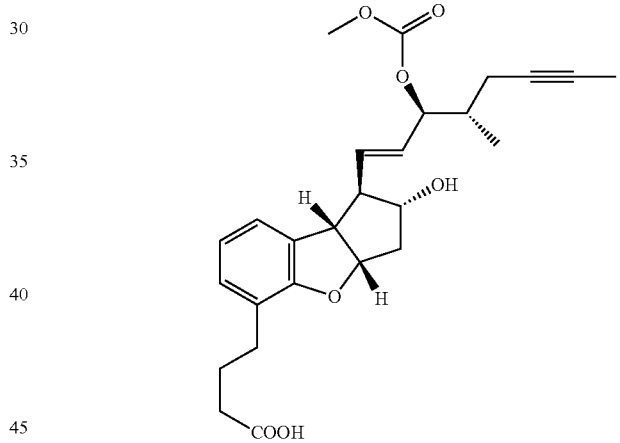

8

Scheme 3. Synthesis of Esuberaprost Side Chain Methyl Carbonate (8)

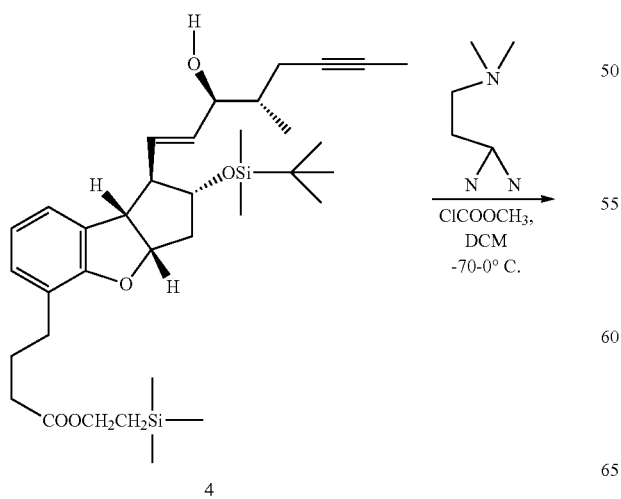

4

ClCOOCH₃,
DCM
-70-0° C.

As shown in Scheme 3, esuberaprost side chain methyl carbamate (8) was also synthesized from TBDMS esuberaprost TMSE ester (4). The methyl carbonate (7) was synthesized from TMSE ester (4) by treating with methyl chloroformate in the presence of N,N,N'N'-tetramethylethylenediamine (TMEDA) in dichloromethane at -70° C. in good yield. The desilylation of compound (7) with tetrabutylammonium fluoride (TBAF) in tetrahydrofuran afforded esuberaprost side chain methyl carbonate (8). This prodrug (8) was characterized by spectral data (IR, $^1$H NMR, $^{13}$C NMR and MS).

Scheme 4. Synthesis of Esuberaprost Glycine Amide (11)

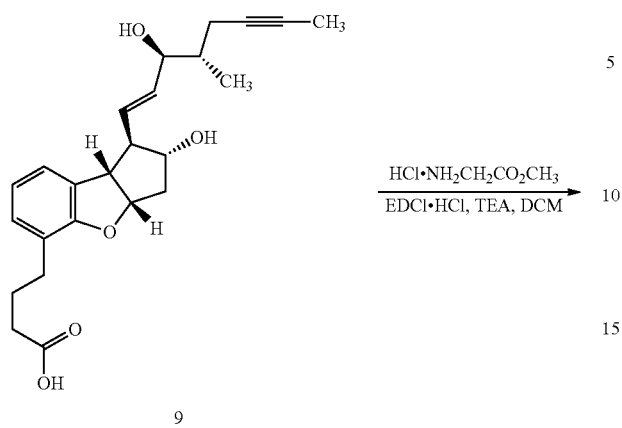

As shown in Scheme 4, esuberaprost glycine amide (11) was synthesized from esuberaprost (9). The esuberaprost (4) was treated with glycine methyl ester hydrochloride in the presence of EDCI.HCl and triethylamine to give amido methyl ester (10). The ester (10) was hydrolyzed with trimethyltin hydroxide to afford the desired esuberaprost glycine amide (11). The prodrug (11) was characterized was characterized by spectral data ($^1$H NMR and MS).

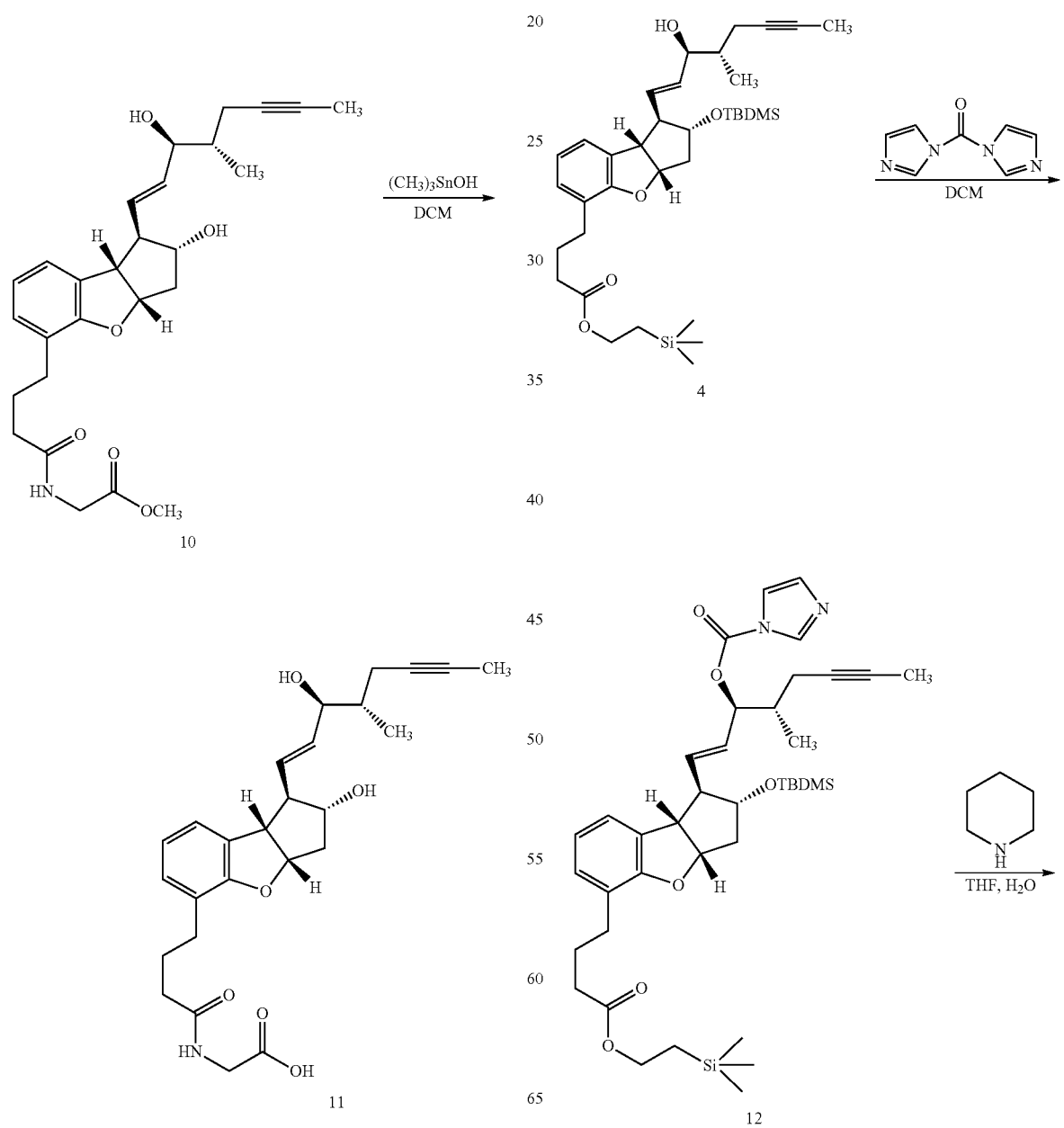

Scheme 5 Synthesis of Esuberaprost Side Chain Piperidine Carbamate (14)

-continued

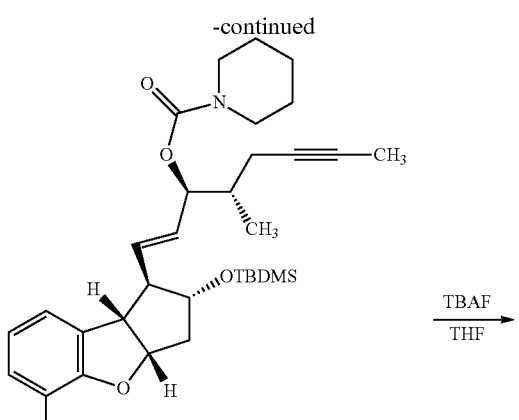

13

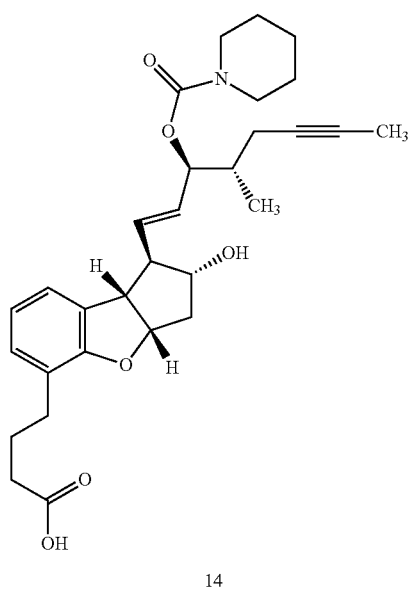 [SMILES: CC#CC[C@H](C)[C@@H](/C=C/[C@@H]1[C@H]2c3cccc(CCCC(=O)O)c3O[C@H]2C[C@H]1O)OC(=O)N1CCCCC1]

14

TBAF
THF
→

As shown in Scheme 5, esuberaprost side chain piperidine carbamate (14) was synthesized from TBDMS esuberaprost TMSE ester (4). The TBDMS esuberaprost TMSE ester (4) was reacted with carbonyldiimidazole (CDI) to obtain carbonylimidazole derivative (12). The activated compound 12 was reacted with piperidine in the presence of water and tetrahydrofuran to obtain piperidine side chain carbamate (13). The TBDMS and TMSE protecting groups of carbamate intermediate (14) were cleaved using tetrabutylammonium fluoride (TBAF) to obtain esuberaprost side chain piperidine carbamate (14) and was characterized by spectral data ($^1$H NMR, $^{13}$C NMR, LC-MS).

The present invention is further illustrated by, though in no way limited to, the following examples.

Example 1: Synthesis of Di-TBDMS Esuberaprost Methanesulfonamide (2)

To a solution of di-TBDMS esuberaprost (1) (0.18 g, 0.287 mmol) in anhydrous tetrahydrofuran (2 mL) was added 1,1'-carbonyldiimidazole (CDI) (0.07 g, 0.432 mmol) in one portion at room temperature under argon. The clear reaction mixture was stirred at room temperature for 30 min and then at 75° C. (oil bath temperature) for 30 min. The reaction mixture was cooled to room temperature and then methansulfonamide (0.082 g, 0.862 mmol) was added in one portion. The reaction mixture was stirred at room temperature until clear solution was obtained. To this clear solution was added a solution of 1,8-diazabicyclo[5.4.0]undec-7-ene (DBU) (0.22 g, 1.44 mmol) in anhydrous tetrahydrofuran (2 mL) under argon. After complete addition, the reaction mixture was stirred at room temperature for 2 h and the reaction was monitored by TLC (MeOH/CH$_2$Cl$_2$, 0.5:9.5). The reaction was not complete. The reaction mixture was continued to stir at room temperature overnight. After 17 h, the reaction was checked by tlc (MeOH/CH$_2$Cl$_2$, 0.5:9.5). The mixture was quenched with water (15 mL) and then extracted with EtOAc (3×15 mL). The combined EtOAc extracts were washed with water (3×15 mL), brine (1×10 mL), dried (Na$_2$SO$_4$), filtered and concentrated in vacuo to give white foamy sticky solid (0.187 g) (Lot #RD-UT-1204-147). The crude product was chromatographed on silica gel (230-400 mesh) (15 g) using CH$_2$Cl$_2$ and 1-8% MeOH/CH$_2$Cl$_2$ to give di-TBDMS esuberaprost methanesulfonamide (2) as a white foamy sticky solid (0.13 g) (Lot #RD-UT-1204-147-C). The pure fraction of 2 (0.02 g) (Lot #RD-UT-1204-147-B) was fully characterized by spectral data (IR, $^1$H NMR, $^{13}$C NMR, DEPT and MS).

TABLE 1

Materials used in Example 1

| Name | MW | Lot No. | Amount | mmol | Eq. |
|---|---|---|---|---|---|
| Di-TBDMS esuberaprost (1) | 627.02 | RD-UT-1161-075-B | 0.18 g | 0.287 | 1.00 |
| 1,1'-Carbonyldiimidazole (CDI) | 162.15 | BCBR6489V | 0.07 g | 0.432 | 1.5 |
| Methanesulfonamide | 95.12 | BCBH0661V | 0.082 g | 0.862 | 3.0 |
| 1,8-Diazabicyclo[5.4.0]-undec-7-ene (DBU) | 152.24 | BCBR7994V | 0.22 g | 1.44 | 5.0 |
| Tetrahydrofuran (anhydrous) | NA | SHBJ0753 | 4.0 mL | NA | NA |
| Silica gel (230-400 mesh) | NA | TA2142885 | 15 g | NA | NA |

The reaction in Example 1 is described in the scheme below:

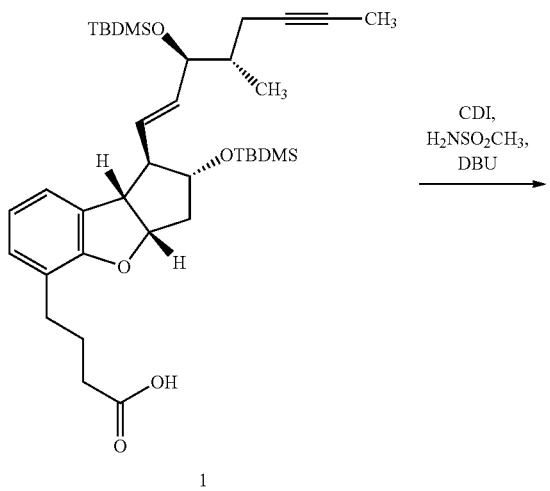

Example 2: Synthesis of Esuberaprost Methanesulfonamide (3)

To a solution of di-TBDMS esuberaprost methanesulfonamide (2) (0.13 g, 0.185 mmol) in anhydrous methanol (2 mL) was added a solution of hydrogen chloride in methanol (1.25 M) (0.40 mL, 0.50 mmol) at room temperature under argon. The reaction mixture was stirred at room temperature for 3 h and checked by TLC (MeoH/CH$_2$Cl$_2$, 0.5:9.5 and 1:9). The reaction was complete. The argon was bubbled slowly through the reaction mixture for 2 min at room temperature to remove excess hydrogen chloride. Then, the mixture was evaporated in vacuo at 30° C. (water bath temperature) to remove the organic volatiles to give crude sulfonamide product (3) as a pale yellow glassy viscous liquid (0.097 g) (Lot #RD-UT-1204-154). The crude product was chromatographed on silica gel (10 g) column using 25-100% EtOAc/Hexane and 5-10% MeOH/EtOAc to give esuberaprost methanesulfonamide (3) as a pale yellow viscous liquid (0.021 g) (Lot #RD-UT-1204-154-A) and (0.041 g) (Lot #RD-UT-1204-154-B). The compound was characterized by spectral data (IR, $^1$H NMR, $^{13}$C NMR, DEPT and MS).

TABLE 2

| Material used in Example 2 | | | | | |
| --- | --- | --- | --- | --- | --- |
| Name | MW | Lot No. | Amount | mmol | Eq. |
| Di-TBDM esuberaprost methansulfonamide (2) | 703.14 | RD-UT-1204-147-C | 0.13 g | 0.185 | 1.00 |
| Hydrogen chloride in methanol (1.25M) | 36.5 | BCBT3427 | 0.40 mL | 0.50 | 2.70 |
| Methanol (anhydrous) | NA | 01949CJ | 2 mL | NA | NA |
| Silica gel (230-400 mesh) | NA | TA2142885 | 10 g | NA | NA |

The reaction in Example 2 is described in the scheme below:

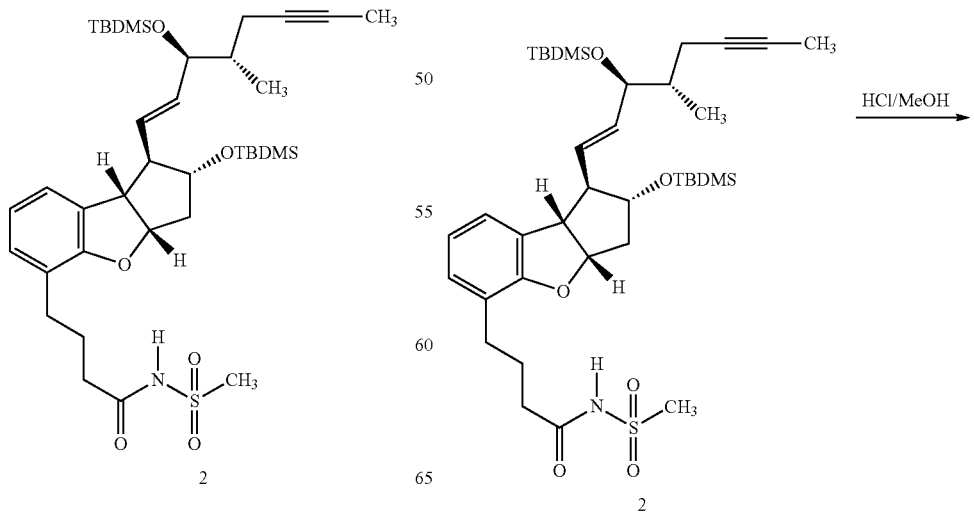

-continued

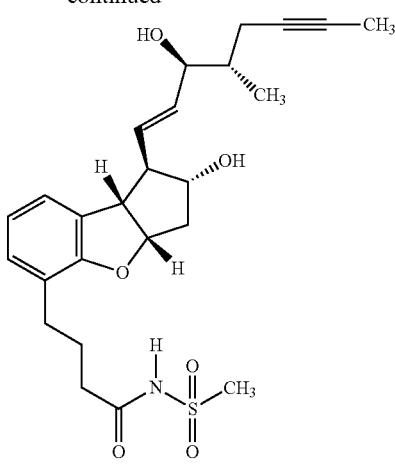

3

Example 3: Synthesis of TBDMS Esuberaprost TMSE Ester Side Chain N,N-Dimethyl Carbamate (5)

TBDMS esuberaprost TMSE ester (4) (100 mg, 0.16 mmol) and pyridine (38.7 mg, 0.49 mmol) were dissolved in anhydrous THF (3 ml) at room temperature under argon. The solution was cooled to 0-5° C., and then 4-nitrophenyl chloroformate (74.3 mg, 0.37 mmol) in THF (1 ml) was added dropwise. The reaction mixture was stirred for 1.5 h and then dimethylamine (22 mg, 0.49 mmol) in THF (0.5 ml) was added. The reaction mixture was continued to stir at 0-5° C. for 1 h and checked TLC (EtOAc/Hexane 1:4), the reaction was complete. The reaction mixture was concentrated in vacuo to obtain crude product. The chromatography of crude product on silica gel using 0-20% EtOAc in hexane afforded desired carbamate (5) (103 mg) (Lot #RD-UT-1199-101A). The TBDMS esuberaprost TMSE ester side chain N,N-dimethyl carbamate (5) was characterized by spectral data ($^1$H NMR and MS).

TABLE 3

Material used in Example 3

| Name | MW | Lot No. | Amount | mmol | Eq. |
|---|---|---|---|---|---|
| TBDMS Esuberaprost TMSE ester (4) | 613.00 | RD-UT-1199-079 | 100.0 mg | 0.16 | 1.0 |
| Pyridine | 79.16 | SHBH7698 | 38.7 mg | 0.49 | 3.0 |
| 4-Nitrophenyl chloroformate | 201.56 | WXBC1772V | 74.3 mg | 0.37 | 2.3 |
| Dimethylamine | 45.08 | SHBG-0756V | 22.0 mg | 0.49 | 3.0 |
| THF | NA | SHBJ0753 | 4.5 ml | NA | NA |

The reaction in Example 3 is described in the scheme below:

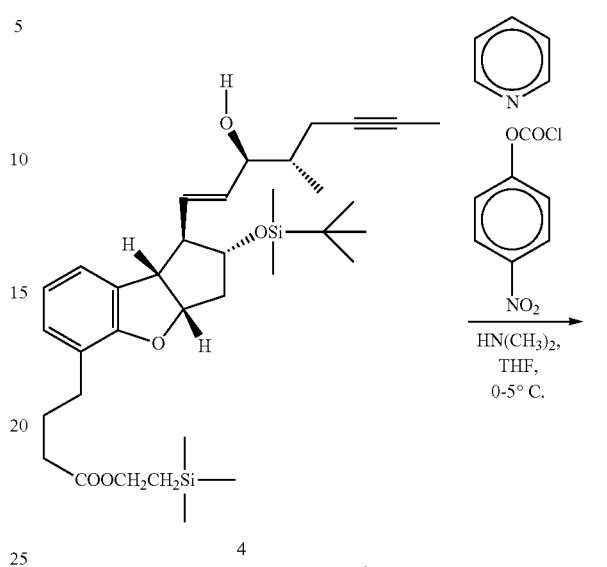

4

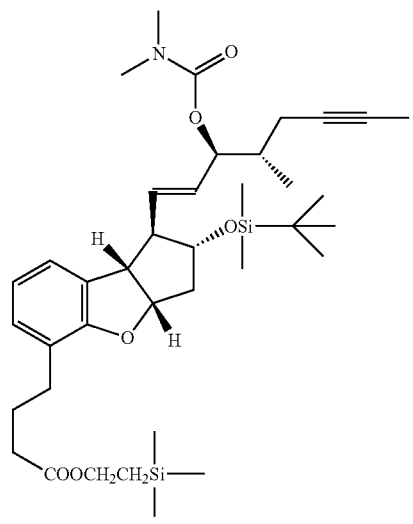

5

Example 4: Synthesis of Esuberaprost Side Chain N,N-Dimethyl Carbamate (6)

The TBDMS esuberaprost TMSE ester side chain N,N-dimethyl carbamate (5) (98 mg, 0.14 mmol) was dissolved in anhydrous THF (10 ml) and TBAF (1.0 M in THF) (0.86 ml, 0.86 mmol) was added dropwise at room temperature under argon with stirring. The progress of reaction was monitored by TLC (EtOAc/Hexane, 1:4, DCM/MeOH, 9:1). The reaction was stopped stirring after 5 h and the solvent was evaporated in vacuo. The residue was dissolved in EtOAc (8 ml) and washed with water (1×5 ml) and brine (2×5 ml), then dried over $Na_2SO_4$ and concentrated in vacuo to give crude product (203 mg). The chromatography of crude product on silica gel with 0-5% MeOH in EtOAc gave desired product compound (6) (119 mg) (Lot #RD-UT-1199-103-1). The second chromatography of the product on silica gel with 0-5% methanol in DCM afforded the pure desired carbamate (6) (39 mg) (Lot #RD-UT-1199-103-2). The esuberaprost side chain N,N-dimethyl carbamate (6) was characterized by spectral data ($^1$H NMR, $^{13}$C NMR, IR and MS).

TABLE 4

| Material used in Example 4 | | | | | |
|---|---|---|---|---|---|
| Name | MW | Lot No. | Amount | mmol | Eq. |
| Alkenyl acetoxycyclopentabenzofuran (5) | 358.42 | RD-UT-1137-178 | 14.2 g | 39.61 | 1.0 |
| Methanol (anhydrous) | NA | T-08-0195 | 150 mL | NA | NA |
| Dichloromethane (anhydrous) | NA | SHBF0333V | 50 mL | NA | NA |
| Sodium borohydride | 37.83 | 0000023281 | 2.99 g | 79.23 | 2.0 |
| Silica gel (230-400 mesh) | NA | 80107 | 622 g | NA | NA |

The reaction in Example 4 is described in the scheme below:

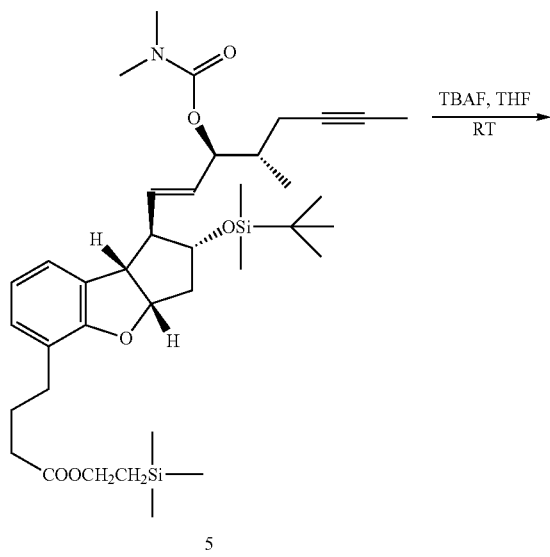

Example 5: Synthesis of TBDMS Esuberaprost TMSE Ester Side Chain Methyl Carbonate (7)

The TBDMS esuberaprost TMSE ester (4) (100 mg, 0.163 mmol) and N,N,N',N'-tetramethylethylenediamine (38 mg, 0.33 mmol) were dissolved in anhydrous DCM (5 ml), the solution was cooled to −70° C. and then methyl chloroformate (31 mg, 0.326 mmol) in anhydrous DCM (1 ml) was added dropwise under argon with stirring. The reaction mixture was stirred for 2 h at this temperature and then at 0° C. for 2 h and the progress of reaction was monitored by TLC (EtOAc/Hexane 1:4). The reaction was not complete. The reaction mixture was re-cooled to −50° C. and additional methyl chloroformate (31 mg, 0.326 mmol) in DCM (1 ml) was added dropwise, then the reaction mixture was stirred for another 2 h. The reaction was complete. The reaction mixture was quenched with water (5 ml) and the organic layer was separated and washed with brine (2×3 ml), then dried over $Na_2SO_4$ and concentrated in vacuo to obtain crude product. The chromatography of the crude product on silica gel using 0-4% EtOAc in hexane afforded pure carbonate (7) (118 mg) (Lot #RD-UT-1199-104). The TBDMS esuberaprost TMSE ester side chain methyl carbonate (7) was characterized by spectral data CH NMR, $^{13}$C NMR, IR and MS).

TABLE 5

| Material used in Example 5 | | | | | |
|---|---|---|---|---|---|
| Name | MW | Lot No. | Amount | mmol | Eq. |
| TRDN Esuberaprost TMSE ester (4) | 613.00 | RD-UT-1199-079 | 100 mg | 0.16 | 1.0 |
| N,N,N',N'-Tetramethylethylenediamine (TMEDA) diamine | 116.21 | 10201026 | 38 mg | 0.33 | 7.0 |
| Methyl chloroformate | 94.50 | STBF9617V | 62 mg | 0.56 | 4.0 |
| DCM (anhydrous) | NA | 53200 | 5 ml | NA | NA |

The reaction in Example 5 is described in the scheme below:

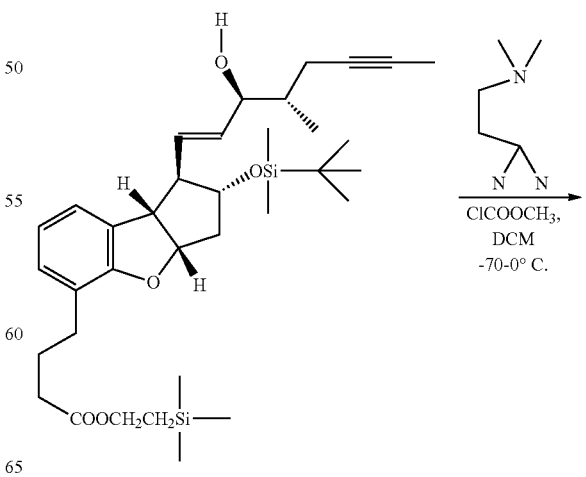

Example 6: Synthesis of Esuberaprost Side Chain Methyl Carbonate (8)

The TBDMS esuberaprost TMSE ester side chain methyl carbonate (7) (110 mg, 0.16 mmol) was dissolved in anhydrous THF (10 ml) and TBAF (1.0 M in THF) (0.98 ml, 0.98 mmol) was added dropwise at room temperature under argon with stirring. The reaction was monitored by TLC (EtOAc/Hexane, 1:4 and DCM/MeOH, 9:1). The reaction was stopped stirring after 1.5 h and the solvent was evaporated in vacuo. The residue was dissolved in EtOAc (8 ml) and washed with water (1×5 ml) and brine (2×5 ml), then dried over $Na_2SO_4$ and concentrated in vacuo to give crude product. The chromatography of crude product on silica gel with 0-5% MeOH in DCM afforded desired carbonate (8) (76 mg) (Lot #RD-UT-1199-105). The esuberaprost side chain methyl carbonate (8) was characterized by spectral data ($^1$H NMR, $^{13}$C NMR, IR and MS).

TABLE 6

Material used in Example 6

| Name | MW | Lot No. | Amount | mmol | Eq. |
|---|---|---|---|---|---|
| TBDMS esuberaprost TMSE ester side chain methyl carbonate (7) | 671.03 | RD-UT-1199-101A | 110 mg | 0.16 | 1.0 |
| TBAF (1.0M in THF) | 261.47 | 09622CH | 0.98 ml | 0.98 | 6.0 |
| THF (anhydrous) | NA | SHBJ0753 | 10 ml | NA | NA |

The reaction in Example 6 is described in the scheme below:

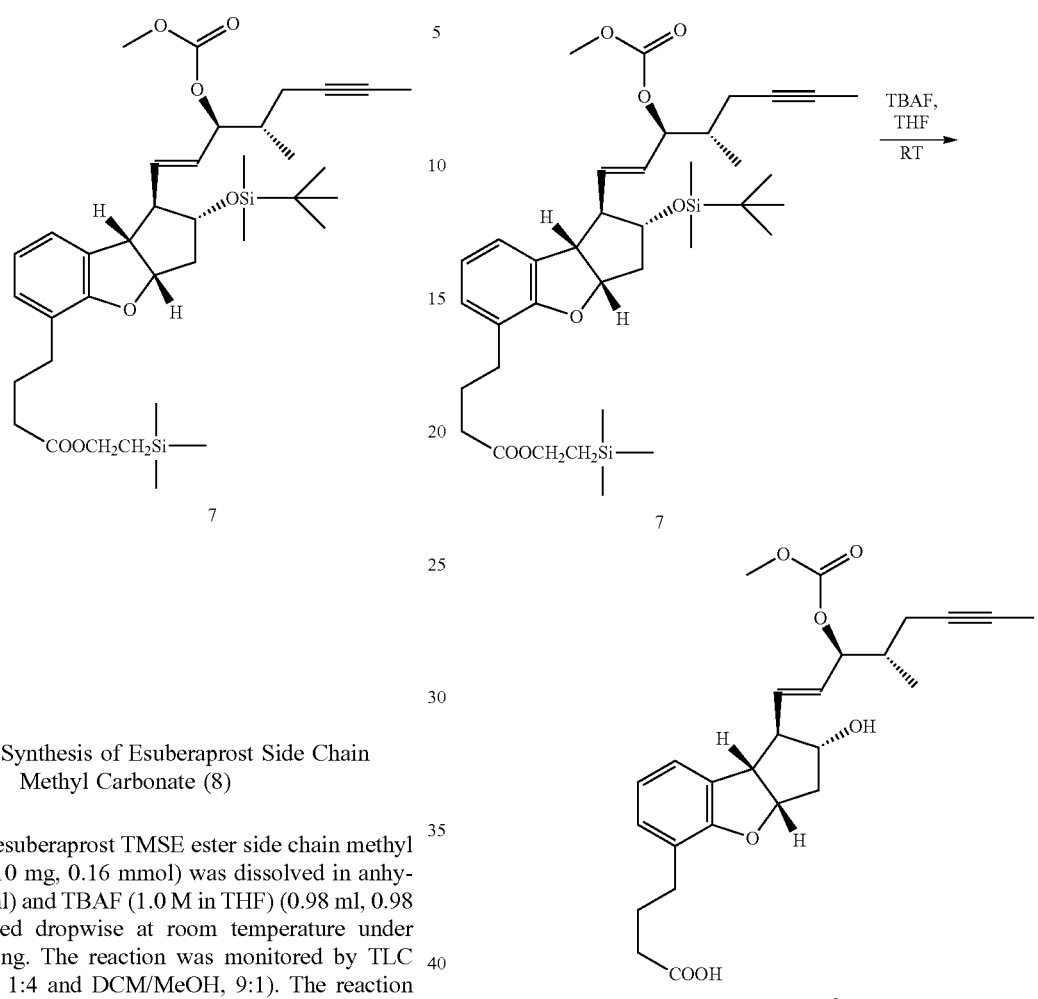

Example 7: Synthesis of Esuberaprost Glycine Amide Methyl Ester (10)

A 50 mL round bottom flask equipped with magnetic stir bar charged with a solution of esuberaprost (9) (0.95 g, 2.38 mmol) in anhydrous DCM (40 mL) under argon. To this solution was added EDCI.HCl (0.68 g, 3.57 mmol) followed by glycine methyl ester hydrochloride (0.30 g, 2.38 mmol) at room temperature under argon. The reaction mixture was stirred for 20 min and then triethylamine (0.072 g, 7.14 mmol) was added. The progress of reaction was monitored by TLC (DCM/MeOH, 9:1). After 3 h, the reaction mixture was quenched with water (20 mL) and the pH was adjusted to 4-5 with 5% HCl. The DCM layer was separated and washed with water (20 mL), brine (20 mL), dried ($Na_2SO_4$), filtered and concentrated in vacuo to obtain crude product. The crude product was purified on silica gel using a gradient solvent of 0-5% methanol in ethyl acetate to give pure esuberaprost glycine amide methyl ester (10) (0.55 g) (Lot #RD-UT-1199-017). The compound was characterized by spectral data ($^1$H NMR and MS).

TABLE 7

Material used in Example 7

| Name | MW | Lot No. | Amount | mmol | Eq. |
|---|---|---|---|---|---|
| Esuberaprost (9) | 398.49 | RD-UT-1199-016 | 0.95 g | 2.38 | 1.0 |
| Glycine methyl ester hydrochlotide | 125.55 | STBD9571V | 0.30 g | 2.38 | 1.0 |
| EDCI•HCl | 191.70 | 6XWHN LD | 0.68 g | 3.57 | 1.5 |
| Triethylamine | 101.19 | SHBF6420V | 0.72 g | 7.14 | 3.0 |
| Dichloromethane (anhydrous) | NA | 53200 | 40 ml | NA | NA |

The reaction in Example 7 is described in the scheme below:

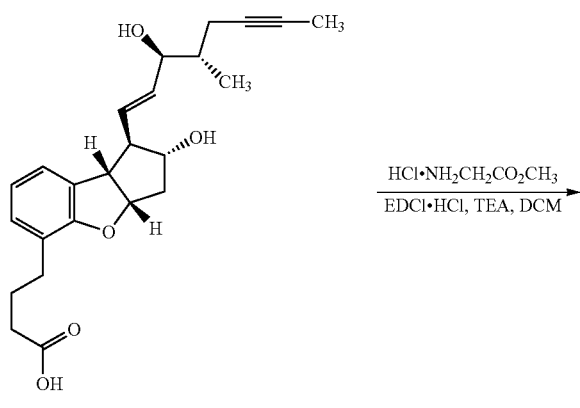

Example 8: Synthesis of Esuberaprost Glycine Amide (11)

The TBDMS esuberaprost TMSE ester side chain methyl carbonate (7) (110 mg, 0.16 mmol) was dissolved in anhydrous THF (10 ml) and TBAF (1.0 M in THF) (0.98 ml, 0.98 mmol) was added dropwise at room temperature under argon with stirring. The reaction was monitored by TLC (EtOAc/Hexane, 1:4 and DCM/MeOH, 9:1). The reaction was stopped stirring after 1.5 h and the solvent was evaporated in vacuo. The residue was dissolved in EtOAc (8 ml) and washed with water (1×5 ml) and brine (2×5 ml), then dried over $Na_2SO_4$ and concentrated in vacuo to give crude product. The chromatography of crude product on silica gel with 0-5% MeOH in DCM afforded desired carbonate (8) (76 mg) (Lot #RD-UT-1199-105). The esuberaprost side chain methyl carbonate (8) was characterized by spectral data ($^1$H NMR, $^{13}$C NMR, IR and MS).

TABLE 6

Material used in Example 6

| Name | MW | Lot No. | Amount | mmol | Eq. |
|---|---|---|---|---|---|
| Esuberaprost glycine amide methyl ester (10) | 469.25 | RD-UT-1199-017 | 80.1 mg | 0.17 | 1.0 |
| Trimethyltinhydroxide | 180.80 | 20205600 | 153.7 mg | 0.85 | 5.0 |
| Dichloroethane (anhydrous) | NA | 12388HU | 20 ml | NA | NA |

The reaction in Example 8 is described in the scheme below:

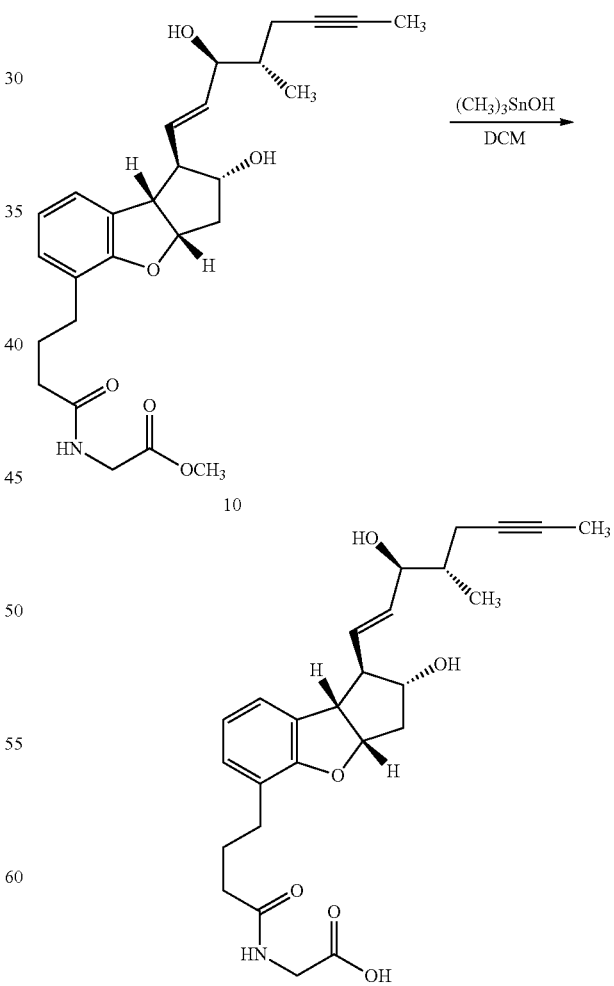

Example 9: Synthesis of TBDMS Esuberaprost TMSE Ester Side Chain Carbonylimidazole (12)

To a solution of TBDMS esuberaprost TMSE ester (4) (20 mg, 0.0326 mmol) in dichloromethane (1.5 mL) was added carbonyldiimidazole (8 mg, 0.0489 mmol). The reaction mixture was stirred at ambient temperature under argon. After 8 h the reaction was found to be 30% complete based on TLC (EtOAc/Hexanes 3:7). The reaction was charged with additional carbonyldiimidazole (32 mg, 0.1956 mmol) in four portion over 40 h. The reaction mixture was quenched with water (1 ml) and the organic layer was separated, washed with brine (1 mL), dried over sodium sulfate and evaporated in vacuo to obtain crude TBDMS esuberaprost TMSE ester carbonylimidazole (12) (32 mg) (Lot #RD-UT-1206-032). The crude product was characterized by $^1$H-NMR.

TABLE 9

Material used in Example 9

| Name | MW | Lot No. | Amount | mmol | Eq. |
|---|---|---|---|---|---|
| TBDMS Esuberaprost TMSE ester (4) | 613.00 | RD-UT-1199-079 | 20 mg | 0.0326 | 1.0 |
| Carbonyldiimidazole (CDI) | 162.15 | BCBR6489V | 40 mg | 0.2445 | 7.5 |
| Dichloromethane (anhydrous) | NA | 53200 | 1.5 mL | NA | NA |

The reaction in Example 9 is described in the scheme below:

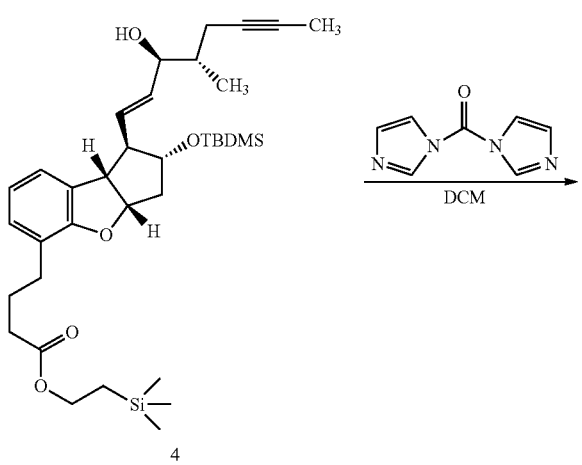

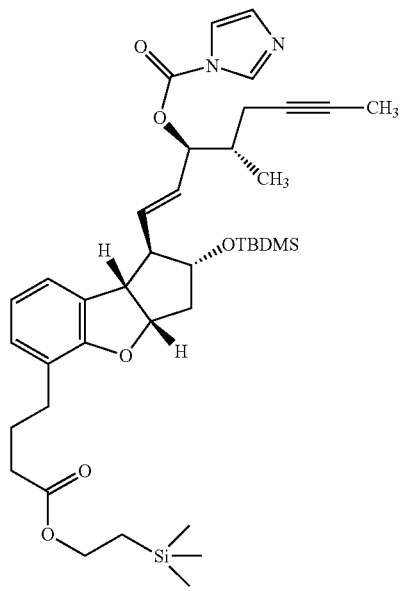

Example 10: Synthesis of TBDMS Esuberaprost TMSE Ester Side Chain Piperidine Carbamate (13)

To a solution of TBDMS esuberaprost TMSE ester side chain carbonylimidazole (12) (30 mg, 0.0424 mmol) in tetrahydrofuran (1 mL) was added piperidine (21 μL, 0.2122 mmol) and water (50 μL). This mixture was stirred at ambient temperature under argon. After 24 h the reaction was found to be 90% complete based on TLC (EtOAc/Hexanes 3:7). The reaction was charged with additional piperidine (21 μL, 0.2122 mmol) and water (100 μL) then stirred for another 6 h. The reaction mixture was evaporated in vacuo and the residue was partitioned between ethyl acetate (1 mL) and water (1 mL). The organic layer was separated, washed with brine (1 mL), dried over sodium sulfate and evaporated in vacuo to obtain crude product (13). This was purified by silica gel column chromatography using ethyl acetate and hexanes (0 to 10%) to obtain pure TBDMS esuberaprost TMSE ester side chain piperidine carbamate (13) (19.4 mg) in 82.1% yield (over two steps) (Lot #RD-UT-1206-040). This product was characterized by $^1$H NMR.

TABLE 10

Material used in Example 10

| Name | MW | Lot No. | Amount | mmol | Eq. |
|---|---|---|---|---|---|
| TBDMS Esuberaprost TMSE ester side chain carbonyl-imidazole (12) | 707.07 | RD-UT-1206-032 | 30 mg | 0.0424 | 1.0 |
| Piperidine | 85.15 | 0295026 | 42 μL | 0.4244 | 10 |
| Tetrahydrofuran | NA | SHBJ0753 | 1 mL | NA | NA |
| Water | NA | Tap | 150 μL | NA | NA |

The reaction in Example 10 is described in the scheme below:

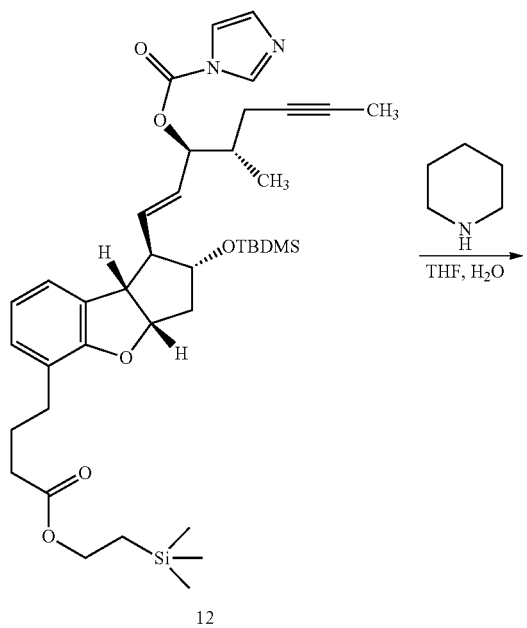

12

13

Example 11: Synthesis of Esuberaprost Side Chain Piperidine Carbamate (14)

To a solution of TBDMS esuberaprost TMSE ester side chain piperidine carbamate (13) (30 mg, 0.0262 mmol) in anhydrous tetrahydrofuran (1 mL) was added tetra-n-butylammonium fluoride solution (157 µL, 0.1574 mmol). This mixture was stirred at ambient temperature under argon. After 2 h, the reaction was found to be complete based on TLC (MeOH/DCM 1:9). The reaction mixture was quenched with water (1 mL) and ethyl acetate (2 mL) was added. The organic layer was separated, and the aqueous layer was extracted with ethyl acetate (2×2 mL). The combined organic layers were washed with brine, dried over sodium sulfate and evaporated in vacuo to obtain esuberaprost side chain piperidine carbamate (14) (20.5 mg) (Lot #RD-UT-1206-049). This was characterized by spectral data ($^1$H NMR, $^{13}$C NMR and MS).

TABLE 11

| Material used in Example 11 | | | | | |
|---|---|---|---|---|---|
| Name | MW | Lot No. | Amount | mmol | Eq. |
| TBDMS Esuberaprost TMSE side chain piperidine carbamate (13) | 724.14 | RD-UT-1206-032 | 19 mg | 0.0262 | 1.0 |
| Tetra butylammonium fluoride (1.0M Solution in THF) | 261.46 | SHBJ8226 | 157 µL | 0.1574 | 6.0 |
| Tetrahydrofuran (anhydrous) | NA | SHBJ0753 | 1 mL | NA | NA |

The reaction in Example 11 is described in the scheme below:

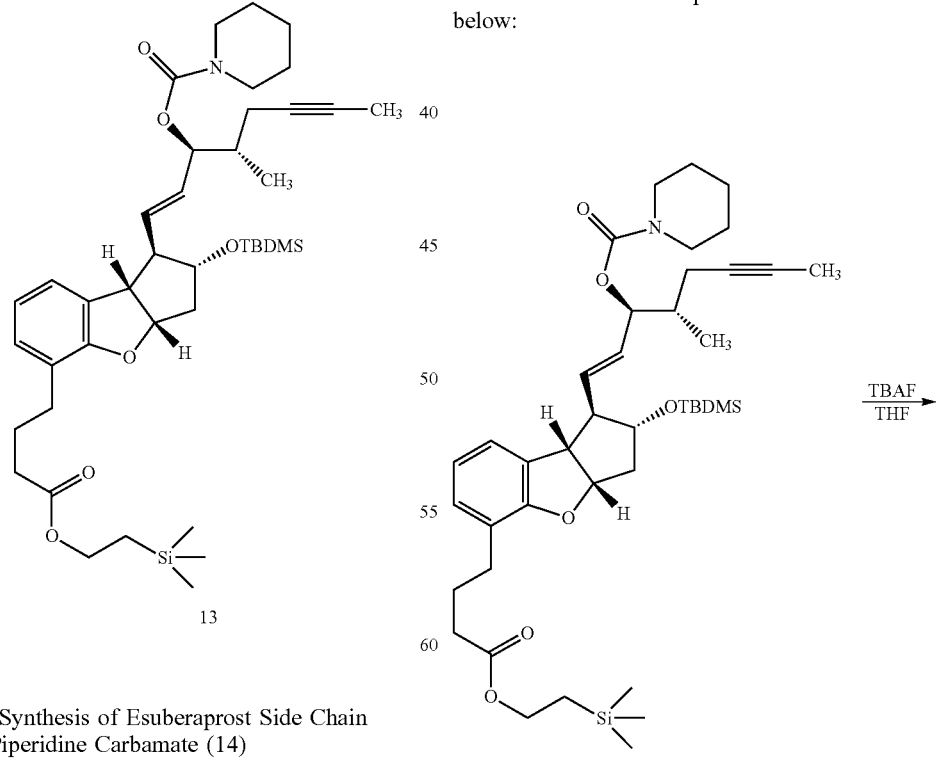

13

Exemplary Esuberaprost prodrugs prepared using methods described above are shown in the Table 12 below.

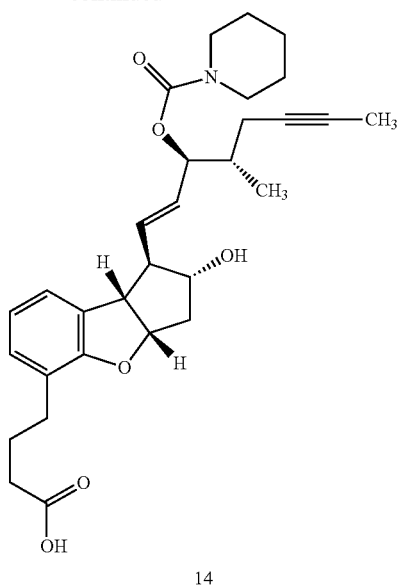

14

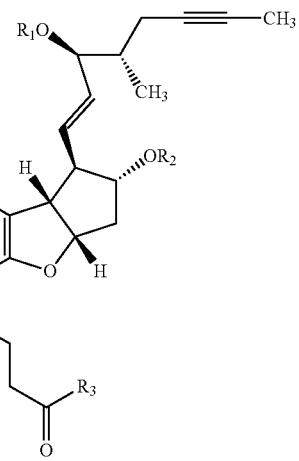

| Name | $R_1$ | $R_2$ | $R_3$ |
|---|---|---|---|
| Esuberaprost Side Chain Methyl Carbonate | $CO_2CH_3$ | H | OH |
| Esuberaprost Cyclopentyl Methyl Carbonate | H | $CO_2CH_3$ | OH |
| Esuberaprost Side Chain Monomethyl Carbamate | $CONHCH_3$ | H | OH |
| Esuberaprost Cyclopentyl Monomethyl Carbamate | H | $CONHCH_3$ | OH |
| Esuberaprost Side Chain Dimethyl Carbamate | $CON(CH_3)_2$ | H | OH |
| Esuberaprost Cyclopentyl Dimethyl Carbamate | H | $CON(CH_3)_2$ | OH |
| Esuberaprost Side Chain Piperidine Carbamate | CON(piperidine) | H | OH |
| Esuberaprost Cyclopentyl Piperidine Carbamate | H | CON(piperidine) | OH |
| Esuberaprost Side Chain Bipiperidine Carbamate | CON(bipiperidine) | H | OH |

-continued

| Name | R₁ | R₂ | R₃ |
|------|----|----|----|
| Esuberaprost Cyclopentyl Bipiperidine Carbamate | H | CON-piperidine-N-piperidine | OH |
| Esuberaprost Side Chain Ethyl Phosphate | (CH$_2$)$_2$OP(O)(OH)$_2$ | H | OH |
| Esuberaprost Cyclopentyl Ethyl Phosphate | H | (CH$_2$)$_2$OP(O)(OH)$_2$ | OH |
| Esuberaprost Side Chain Phosphate | P(O)(OH)$_2$ | H | OH |
| Esuberaprost Cyclopentyl Phosphate | H | P(O)(OH)$_2$ | OH |
| Esuberaprost Cyclic Carbonate R₁ and R₂ connected to carbonyl to make cyclic carbonate | | carbonyl (C=O) linking R₁ and R₂ | OH |
| Esuberaprost Cyclic Phosphate R₁ and R₂ connected to phophosrous to make cyclic phosphate | | P(=O)(OH) linking R₁ and R₂ | OH |
| Esuberaprost alkyl or aryl sulfonamide | H | H | NHSO$_2$R' R' = methyl, ethyl, aryl, substituted aryl etc. |
| Esuberaprost Carboxylic Acid Amides of Amino Acids | | | |
| Esuberaprost Glycine Amide | H | H | Glycine |
| Esuberaprost Alanine Amide | H | H | Alanine |
| Esuberaprost Arginine Amide | H | H | Arginine |
| Esuberaprost Asparagine Amide | H | H | Asparagine |
| Esuberaprost Aspartic Acid Amide | H | H | Aspartic acid |
| Esuberaprost Cystein Amide | H | H | Cysteine |
| Esuberaprost Glutamine Amide | H | H | Glutamine |
| Esuberaprost Glutamic Amide | H | H | Glutamic acid |
| Esuberaprost Histidine Amide | H | H | Histidine |
| Esuberaprost Isoleucine Amide | H | H | Isoleucine |
| Esuberaprost Leucine Amide | H | H | Leucine |
| Esuberaprost Lysine Amide | H | H | Lysine |
| Esuberaprost Methionine Amide | H | H | Methionine |
| Esuberaprost Phenylalanine Amide | H | H | Phenylalanine |

| Name | R₁ | R₂ | R₃ |
| --- | --- | --- | --- |
| Esuberaprost Serine Amide | H | H | Serine |
| Esuberaprost Tryptophane Amide | H | H | Tryptophan |
| Esuberaprost Threonine Amide | H | H | Threonine |
| Esuberaprost Tyrosine Amide | H | H | Tyrosine |
| Esuberaprost Valine Amide | H | H | Valine |
| Esuberaprost Citrilline Amide | H | H | Citrulline |
| Esuberaprost Ornithine Amide | H | H | Ornithine |
| Esuberaprost Side Chain Esters of Amino Acids | | | |
| Esuberaprost Glycine Ester | Glycine | H | OH |
| Esuberaprost Alanine Ester | Alanine | H | OH |
| Esuberaprost Arginine Ester | Arginine | H | OH |
| Esuberaprost Asparagine Ester | Asparagine | H | OH |
| Esuberaprost Aspartic Acid Ester | Aspartic acid | H | OH |
| Esuberaprost Cystein Ester | Cystein | H | OH |
| Esuberaprost Glutamine Ester | Glutamine | H | OH |
| Esuberaprost Glutamic Ester | Glutamic acid | H | OH |
| Esuberaprost Histidine Ester | Histidine | H | OH |
| Esuberaprost Isoleucine Ester | Isoleucine | H | OH |
| Esuberaprost Leucine Ester | Leucine | H | OH |
| Esuberaprost Lysine Ester | Lysine | H | OH |
| Esuberaprost Methionine Ester | Methionine | H | OH |
| Esuberaprost Phenylalanine Ester | Phenylalanine | H | OH |
| Esuberaprost Serine Ester | Serine | H | OH |
| Esuberaprost Tryptophane Ester | Tryptophan | H | OH |
| Esuberaprost Threonine Ester | Threonine | H | OH |
| Esuberaprost Tyrosine Ester | Tyrosine | H | OH |
| Esuberaprost Valine Ester | Valine | H | OH |
| Esuberaprost Citrilline Ester | Citrulline | H | OH |
| Esuberaprost Ornithine Ester | Ornithine | H | OH |
| Esuberaprost Cyclopentyl Esters of Amino Acids | | | |
| Esuberaprost Glycine Ester | H | Glycine | OH |
| Esuberaprost Alanine Ester | H | Alanine | OH |
| Esuberaprost Arginine Ester | H | Arginine | OH |
| Esuberaprost Asparagine Ester | H | Asparagine | OH |
| Esuberaprost Aspartic Acid Ester | H | Aspartic acid | OH |

-continued

| Name | R₁ | R₂ | R₃ |
|---|---|---|---|
| Esuberaprost Cystein Ester | H | Cysteine | OH |
| Esuberaprost Glutamine Ester | H | Glutamine | OH |
| Esuberaprost Glutamic Ester | H | Glutamic acid | OH |
| Esuberaprost Histidine Ester | H | Histidine | OH |
| Esuberaprost Isoleucine Ester | H | Isoleucine | OH |
| Esuberaprost Leucine Ester | H | Leucine | OH |
| Esuberaprost Lysine Ester | H | Lysine | OH |
| Esuberaprost Methionine Ester | H | Methionine | OH |
| Esuberaprost Phenylalanine Ester | H | Phenylalanine | OH |
| Esuberaprost Serine Ester | H | Serine | OH |
| Esuberaprost Tryptophane Ester | H | Tryptophan | OH |
| Esuberaprost Threonine Ester | H | Threonine | OH |
| Esuberaprost Tyrosine Ester | H | Tyrosine | OH |
| Esuberaprost Valine Ester | H | Valine | OH |
| Esuberaprost Citrilline Ester | H | Citrulline | OH |
| Esuberaprost Ornithine Ester | H | Ornithine | OH |

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for the preparation of a compound of Formula (VI):

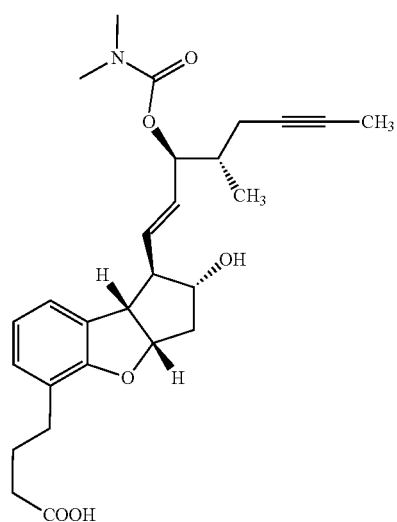

Formula (VI)

comprising:

(a) reacting a compound of Formula (IV)

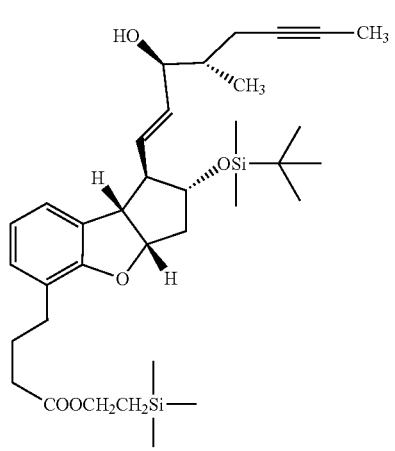

Formula (IV)

with 4-nitrophenyl chloroformate, optionally in the presence of excess of at least one amine base to form a compound of Formula (V);

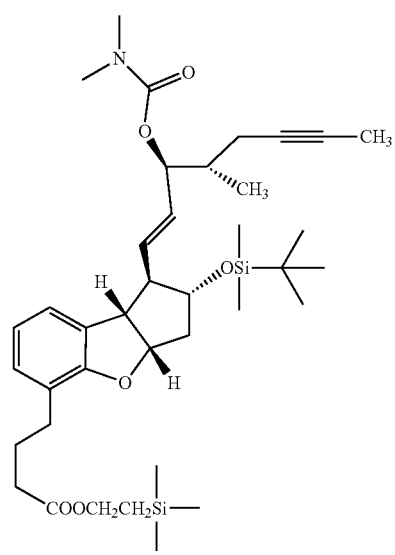

Formula (V)

(b) desilylating the compound of Formula (V) of step (a) to form the compound of Formula (VI).

2. The process of claim 1, wherein the amine base comprises pyridine and dimethylamine.

3. A process for the preparation of a compound of Formula (VIII):

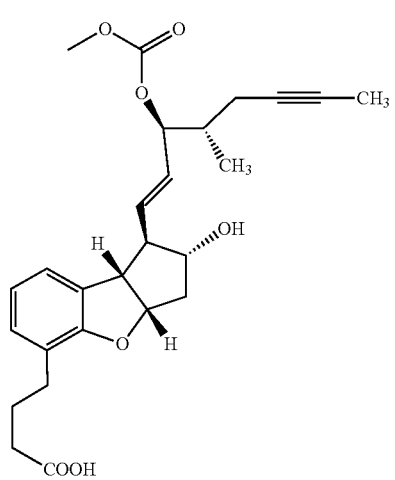

Formula (VIII)

comprising:

(a) reacting a compound of Formula (IV)

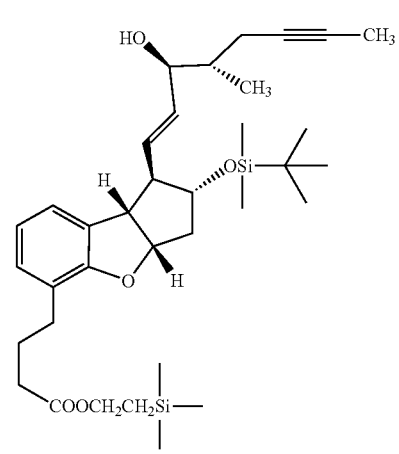

Formula (IV)

with methyl chloroformate, optionally in the presence of at least one amine base to form a compound of Formula (VII);

Formula (VII)

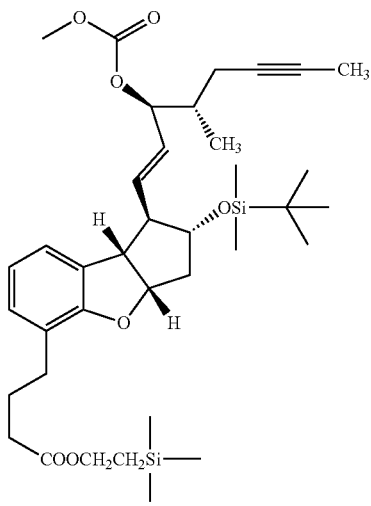

(b) desilylating the compound of Formula (VII) of step (a) to form the compound of Formula (VIII).

4. The process of claim 3, wherein the amine base is N,N,N',N'-tetramethylethylenediamine.

5. A process for the preparation of a compound of Formula (XIV):

Formula (XIV)

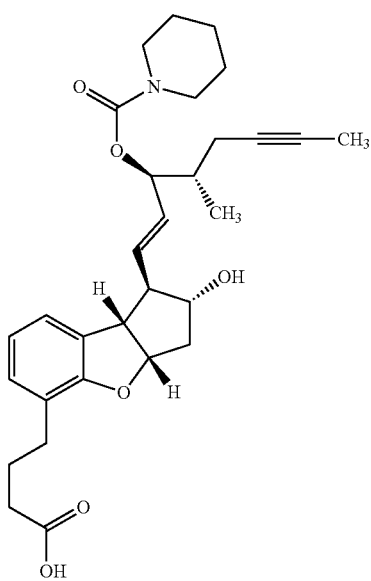

comprising:

(a) reacting a compound of Formula (IV)

Formula (IV)

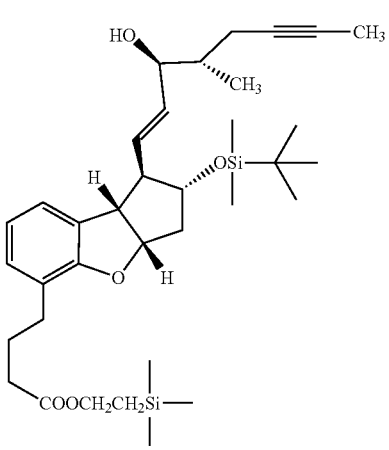

with carbonyldiimidazole to form a compound of Formula (XII);

Formula (XII)

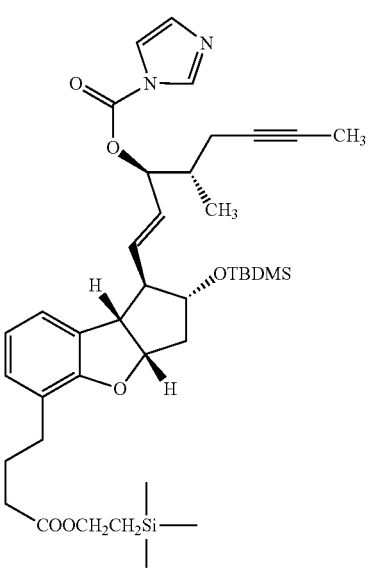

(b) reacting a compound of Formula (XII) with piperidine to form a compound of Formula (XIII);
Formula (XIII)
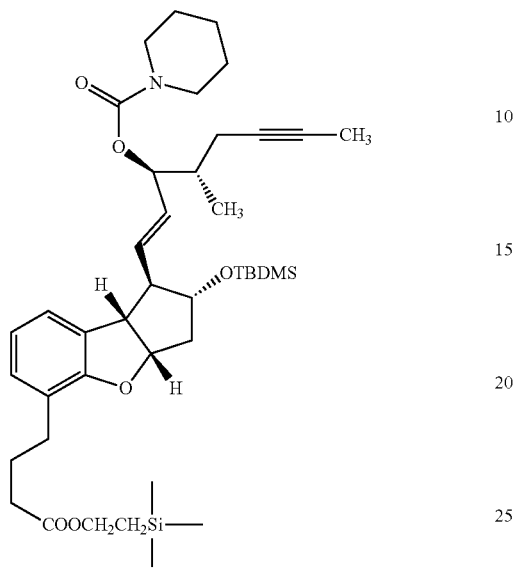
(c) desilylating the compound of Formula (XIII) of step (b) to form the compound of Formula (XIV).
* * * * *